United States Patent
Yamada

(10) Patent No.: US 11,224,331 B2
(45) Date of Patent: Jan. 18, 2022

(54) ADVANCE AND RETREAT ASSISTING TOOL FOR TREATMENT INSTRUMENT AND ENDOSCOPE SYSTEM

(71) Applicant: OLYMPUS CORPORATION, Tokyo (JP)

(72) Inventor: Tetsuhiro Yamada, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 421 days.

(21) Appl. No.: 16/281,484

(22) Filed: Feb. 21, 2019

(65) Prior Publication Data

US 2019/0174996 A1 Jun. 13, 2019

Related U.S. Application Data

(63) Continuation of application No. PCT/JP2017/025402, filed on Jul. 12, 2017.

(30) Foreign Application Priority Data

Aug. 31, 2016 (JP) .............................. JP2016-169315

(51) Int. Cl.
*A61B 1/00* (2006.01)
*A61B 1/018* (2006.01)

(52) U.S. Cl.
CPC .......... *A61B 1/00133* (2013.01); *A61B 1/018* (2013.01)

(58) Field of Classification Search
None
See application file for complete search history.

(56) References Cited

U.S. PATENT DOCUMENTS

2005/0119522 A1 6/2005 Okada
2005/0192475 A1 9/2005 Okada
(Continued)

FOREIGN PATENT DOCUMENTS

| JP | S57-117824 A | 7/1982 |
| JP | 5670002 B1 | 2/2015 |
| WO | WO 2016/098566 A1 | 6/2016 |

OTHER PUBLICATIONS

International Search Report dated Oct. 10, 2017 issued in PCT/JP2017/025402.
(Continued)

*Primary Examiner* — Timothy J Neal
(74) *Attorney, Agent, or Firm* — Scully, Scott, Murphy & Presser, P.C.

(57) ABSTRACT

An advance and retreat assisting tool for a treatment instrument includes: a base; an attaching portion; a first cylinder which is attached to the base; a second cylinder which has a fixing portion fixing the treatment instrument and slides in an advance and retreat direction with respect to the first cylinder along a center axis of the first cylinder; an advance and retreat mechanism which advances and retreats the second cylinder along the center axis with respect to the first cylinder by rotation; and an assisting portion which urges the second cylinder in a predetermined direction along the center axis with respect to the base with an urging force smaller than a resistance force when the second cylinder slides and assists the rotation of the advance and retreat mechanism when the advance and retreat mechanism rotates in one direction.

20 Claims, 23 Drawing Sheets

(56) References Cited

U.S. PATENT DOCUMENTS

2010/0228084 A1    9/2010  Sato et al.
2014/0221739 A1*  8/2014  Yamada ........... A61B 17/00234
                                                    600/106
2015/0119641 A1*  4/2015  Yamada ........... A61B 17/00234
                                                    600/106

OTHER PUBLICATIONS

Japanese Office Action dated May 15, 2018 in Japanese Patent Application No. 2018-511781.
English translation of International Preliminary Report on Patentability dated Mar. 14, 2019 together with the Written Opinion received in related International Application No. PCT/JP2017/025402.

* cited by examiner

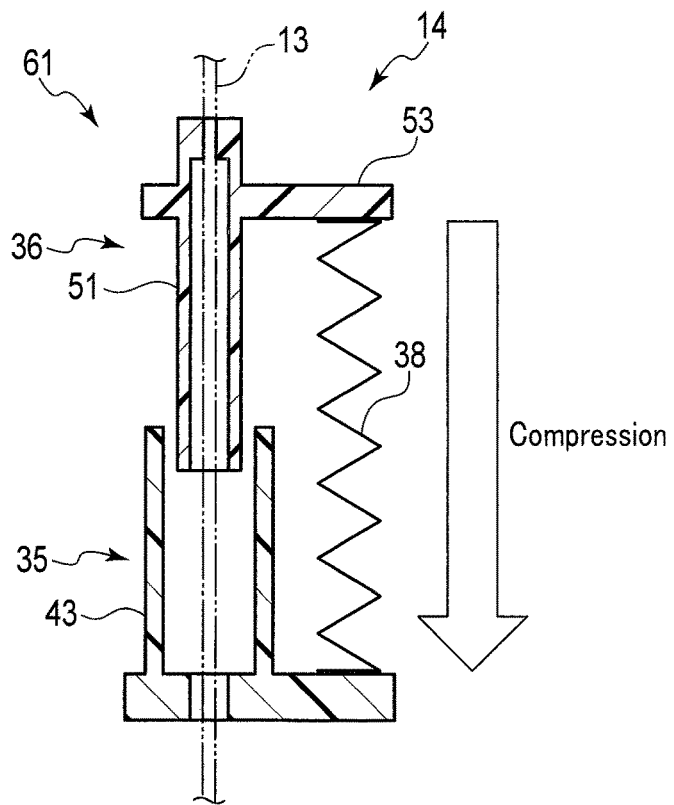
F I G. 12
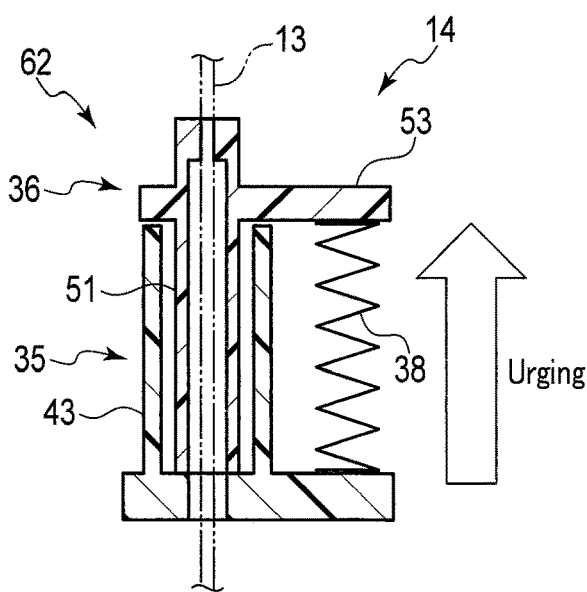
F I G. 13

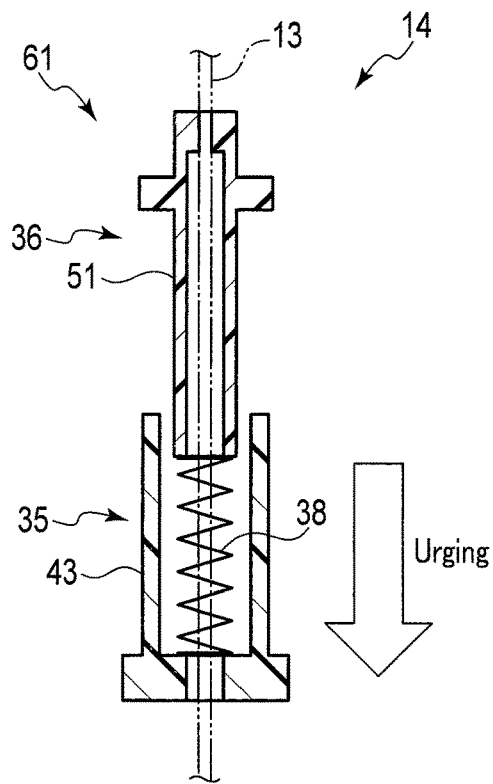
F I G. 14
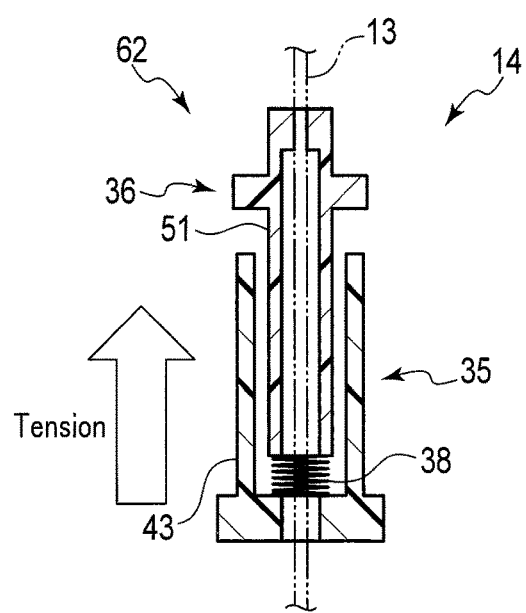
F I G. 15

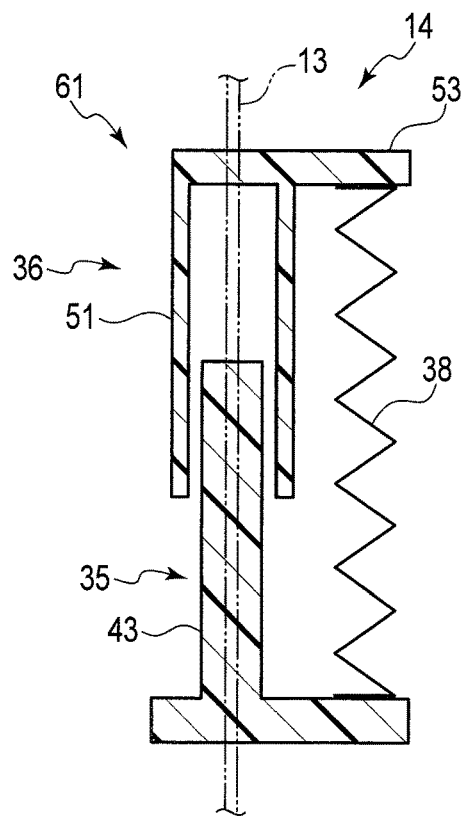
F I G. 19
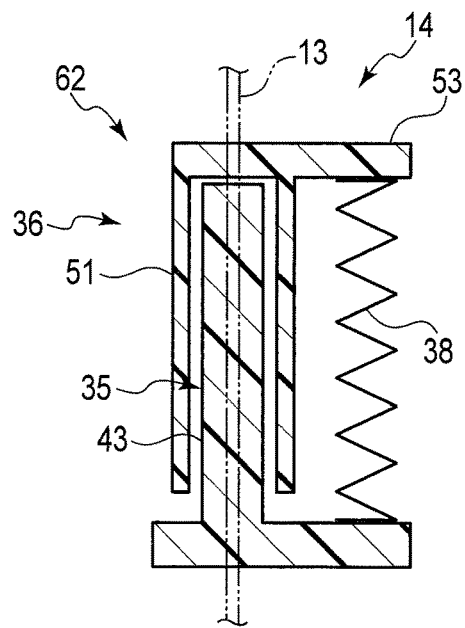
F I G. 20

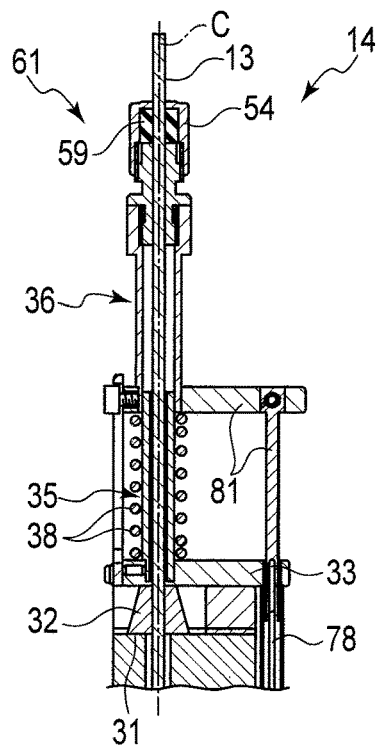
F I G. 21
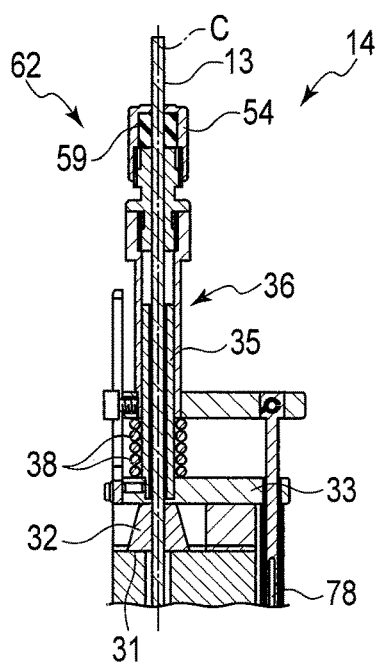
F I G. 22

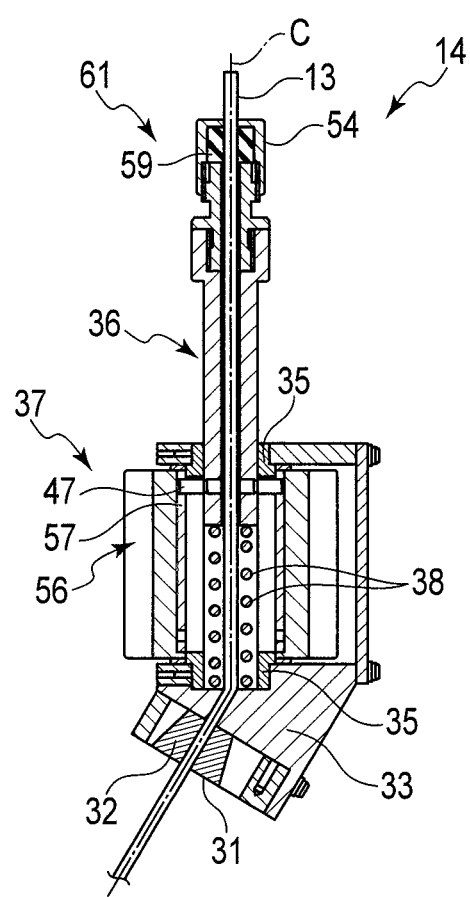
F I G. 27

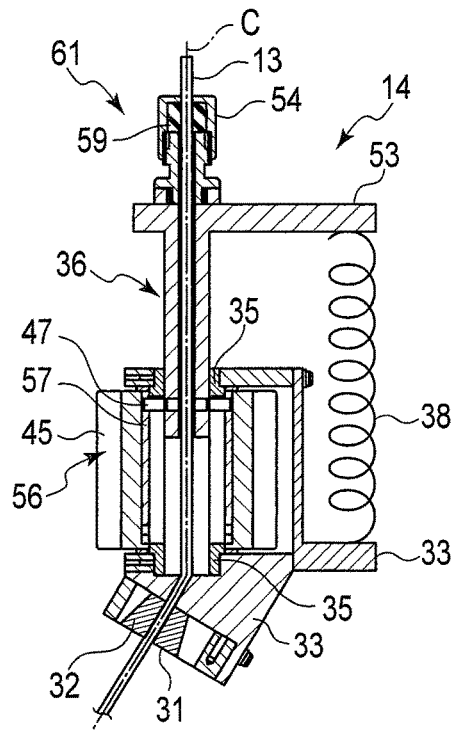
F I G. 28
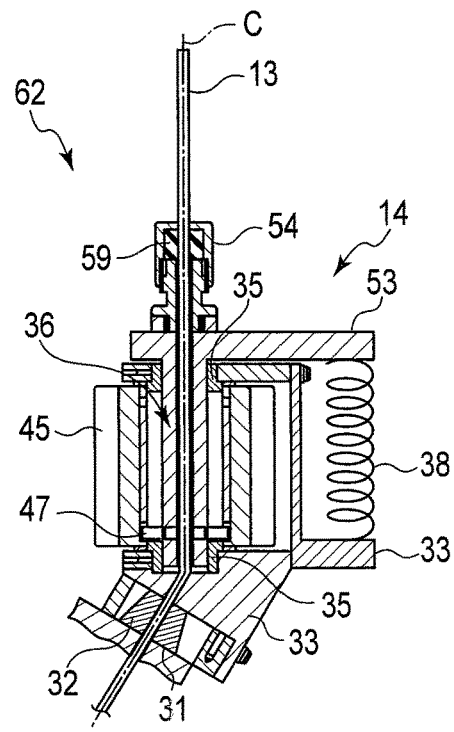
F I G. 29

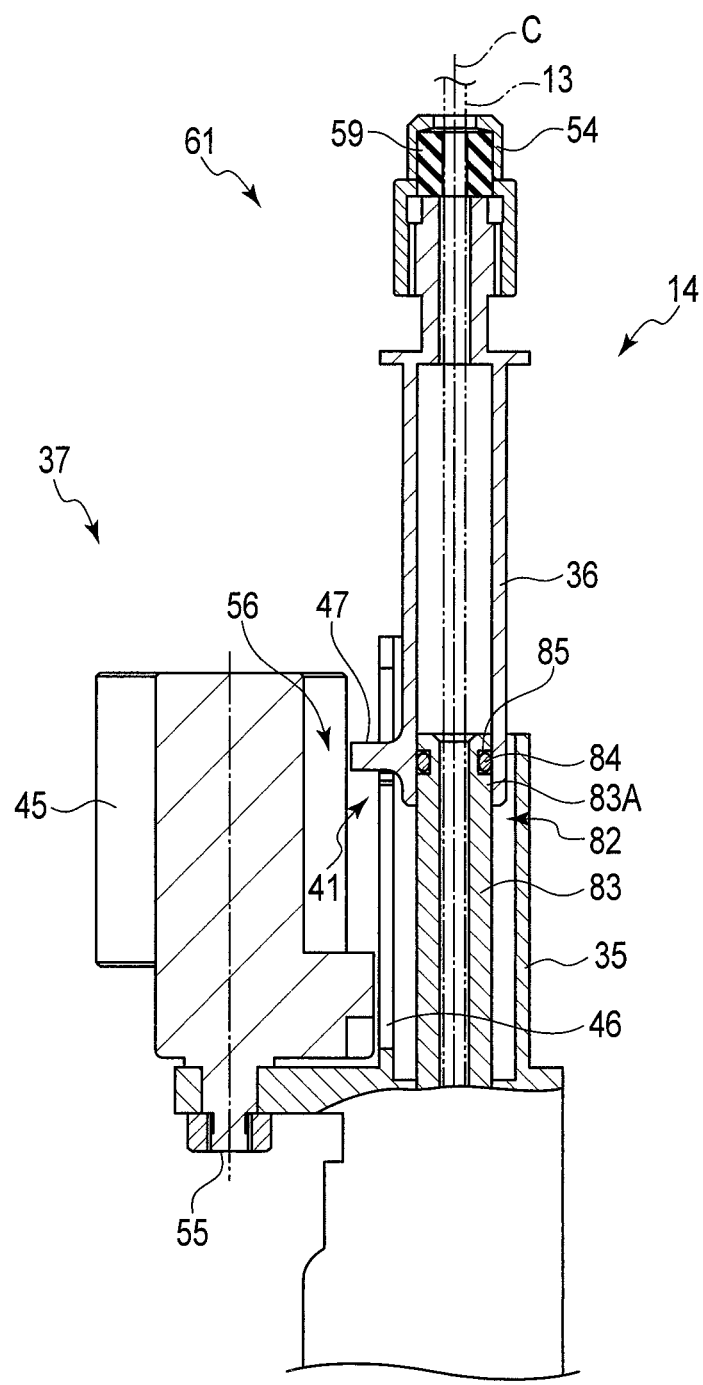
F I G. 30

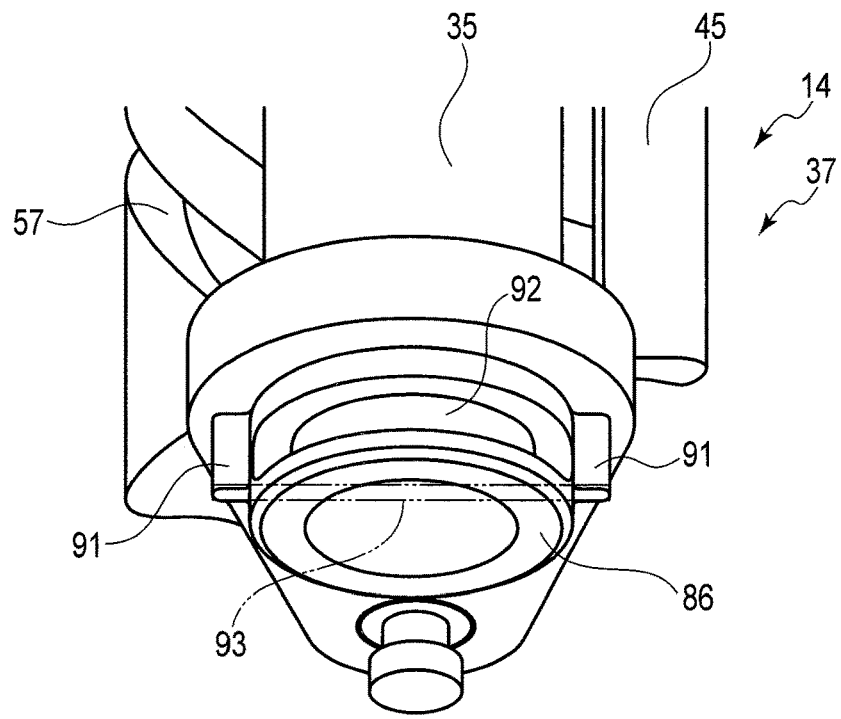
F I G. 31
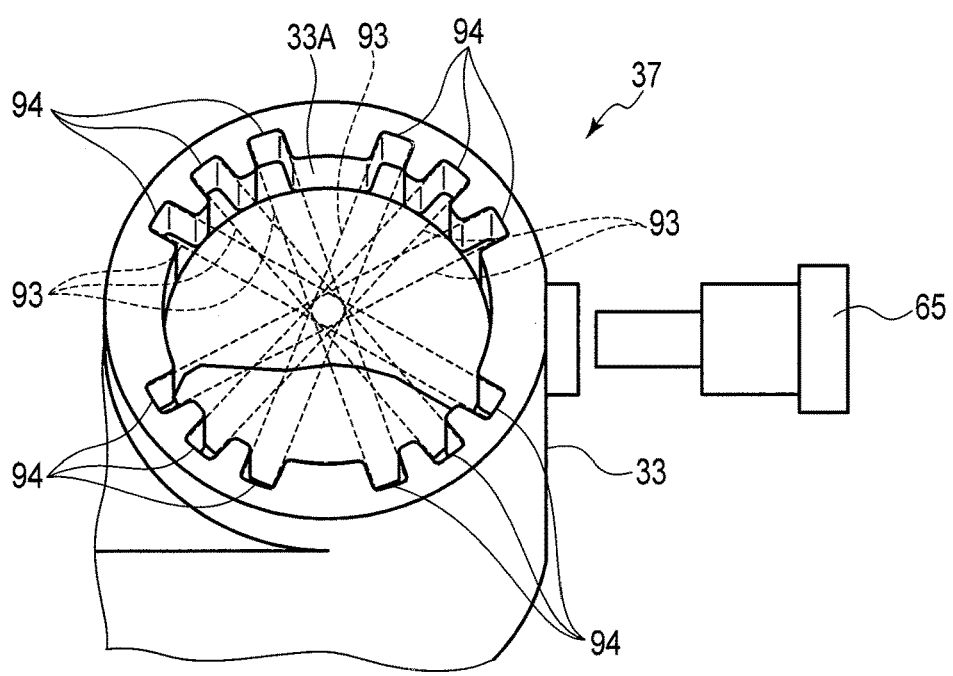
F I G. 32

ADVANCE AND RETREAT ASSISTING TOOL FOR TREATMENT INSTRUMENT AND ENDOSCOPE SYSTEM

CROSS-REFERENCE TO RELATED APPLICATIONS

This application is a Continuation Application of PCT Application No. PCT/JP2017/025402, filed Jul. 12, 2017 and based upon and claiming the benefit of priority from prior Japanese Patent Application No. 2016-169315, filed Aug. 31, 2016, the entire contents of all of which are incorporated herein by reference.

FIELD

The present invention relates to an advance and retreat assisting tool for a treatment instrument for advancing and retreating the treatment instrument.

BACKGROUND

For example, Patent Literature 1 discloses an advance and retreat assisting tool for a treatment instrument passing through an endoscope.

CITATION LIST

Patent Literature

Patent Literature 1: Japanese Patent No. 5670002B

SUMMARY

An advance and retreat assisting tool for a treatment instrument according to an aspect of the present invention includes: a base which has a through-hole; an attaching portion which attaches the base to an endoscope such that the through-hole faces a treatment instrument insertion port of the endoscope; a first cylinder which is attached to the base such that an inner portion thereof is in communication with the through-hole; a second cylinder which has a fixing portion fixing the treatment instrument inserted into the treatment instrument insertion port and slides in an advance and retreat direction with respect to the first cylinder along a center axis of the first cylinder; an advance and retreat mechanism which advances and retreats the second cylinder along the center axis with respect to the first cylinder by rotation; and an assisting portion which urges the second cylinder in a predetermined direction along the center axis with respect to the base with an urging force smaller than a resistance force when the second cylinder slides and assists the rotation of the advance and retreat mechanism when the advance and retreat mechanism rotates in one direction.

BRIEF DESCRIPTION OF THE DRAWINGS

FIG. 12 is a side view schematically showing an assisting portion of an advance and retreat assisting tool of an endoscope system according to a fifth modified example in a state where a second cylinder is at a protruding position.

FIG. 13 is a side view schematically showing the assisting portion of the advance and retreat assisting tool of the endoscope system according to the fifth modified example in a state where the second cylinder is at a received position.

FIG. 14 is a side view schematically showing an assisting portion of an advance and retreat assisting tool of an endoscope system according to a sixth modified example in a state where a second cylinder is at a protruding position.

FIG. 15 is a side view schematically showing the assisting portion of the advance and retreat assisting tool of the endoscope system according to the sixth modified example in a state where the second cylinder is at a received position.

FIG. 19 is a side view schematically showing an advance and retreat assisting tool of an endoscope system according to a ninth modified example in a state where a second cylinder is at a protruding position.

FIG. 20 is a side view schematically showing the advance and retreat assisting tool of the endoscope system according to the ninth modified example in a state where the second cylinder is at a received position.

FIG. 21 is a cross-sectional view showing an advance and retreat assisting tool of an endoscope system according to a tenth modified example in a state where a second cylinder is at a protruding position.

FIG. 22 is a cross-sectional view showing the advance and retreat assisting tool of the endoscope system according to the tenth modified example in a state where the second cylinder is at a received position.

FIG. 27 is a cross-sectional view showing an advance and retreat assisting tool of an endoscope system according to an eleventh modified example in a state where a second cylinder is at a protruding position.

FIG. 28 is a cross-sectional view showing an advance and retreat assisting tool of an endoscope system according to a further modification of the eleventh modified example in a state where a second cylinder is at a protruding position.

FIG. 29 is a cross-sectional view showing the advance and retreat assisting tool of the endoscope system according to the further modification of the eleventh modified example in a state where the second cylinder is at a received position.

FIG. 30 is a cross-sectional view showing an advance and retreat assisting tool of an endoscope system according to a twelfth modified example in a state where a second cylinder is at a protruding position.

FIG. 31 is a perspective view showing a moving unit of an advance and retreat assisting tool of an endoscope system according to a second embodiment.

FIG. 32 is a perspective view showing a base and a fixing member of the endoscope system shown in FIG. 31.

DETAILED DESCRIPTION

Hereinafter, embodiments of the present invention will be described with reference to the drawings. An endoscope of an endoscope system to be described below is inserted into and used in a hole (body cavity) of a medical examinee (subject). An advance and retreat assisting tool 14 (advance and retreat assisting tool for a treatment instrument) applied to an endoscope system 11 is used to finely adjust a position, in a longitudinal direction, of a treatment instrument 13 passing through the inside of a treatment instrument insertion channel 26 of the endoscope, and can finely adjust the position of the treatment instrument 13 in the longitudinal direction by a user's operation.

First Embodiment

Figure 1:
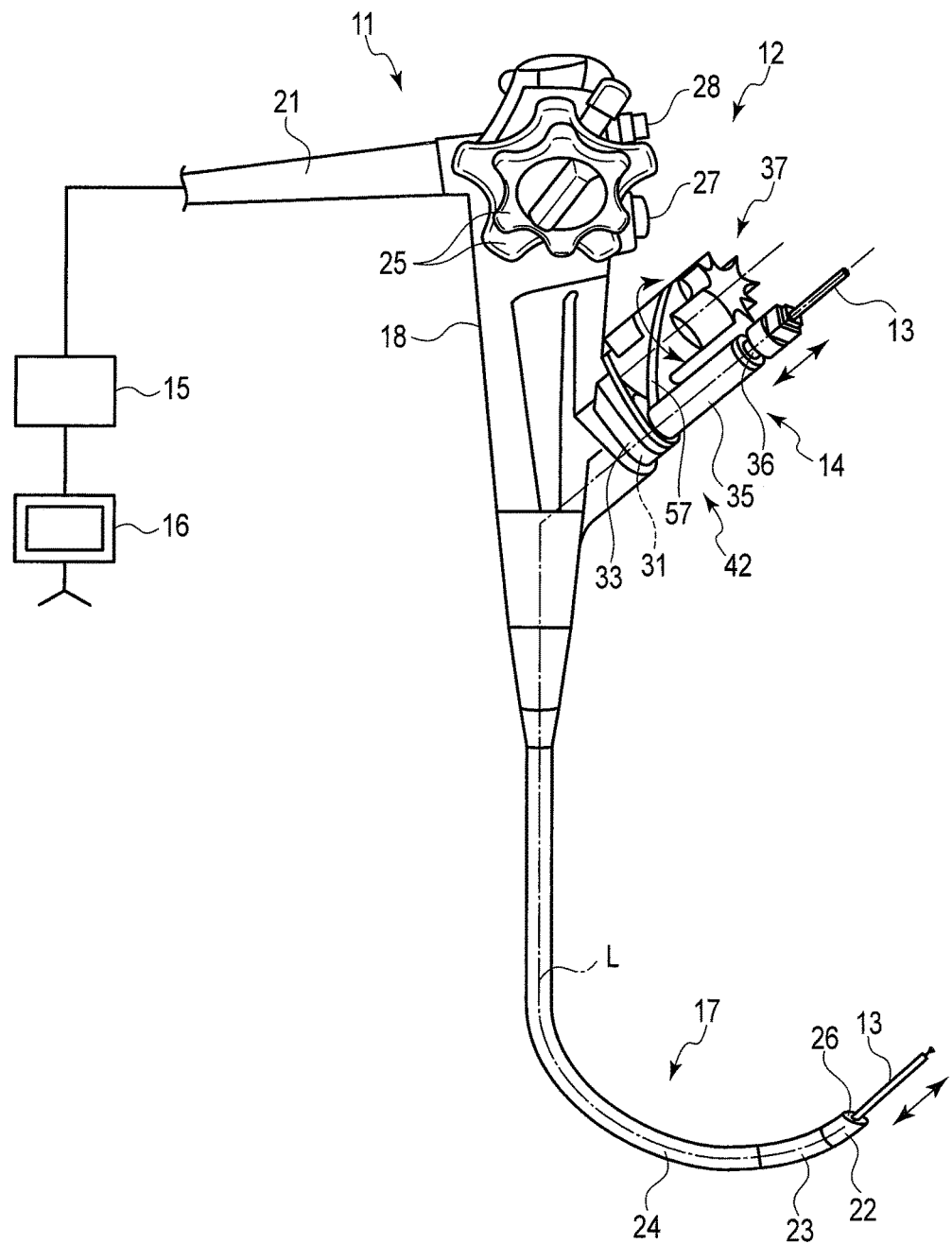
FIG. 1 is a schematic view showing an endoscope system and an endoscope according to a first embodiment.

An endoscope system 11 according to a first embodiment will be described with reference to FIGS. 1 to 6. As shown in FIG. 1, the endoscope system 11 includes an endoscope 12, a treatment instrument 13 passing through the inside of the endoscope 12, an advance and retreat assisting tool 14 attached to the endoscope 12, an endoscope controller 15 (image processing portion) performing image processing based on an image of an object captured by the endoscope 12, and a display portion 16 (monitor) displaying a video generated by the image processing in the endoscope controller 15.

As shown in FIG. 1, the endoscope 12 (insertion device) includes an insertion portion 17 inserted into a duct such as a lumen of a subject in a longitudinal direction L, an operation portion 18 provided at a proximal end of the insertion portion 17 and grasped by a user, a universal cord 21 extending from the operation portion 18, and a distal end constituting portion 22 provided on a distal end side of the insertion portion 17 and being rigid.

As shown in FIG. 1, the insertion portion 17 defines the longitudinal direction L by a distal end and a proximal end thereof. As shown in FIG. 1, the insertion portion 17 includes the distal end constituting portion 22, a bending portion 23, and a tube portion 24 in order from the distal end thereof toward the proximal end thereof. The tube portion 24 has flexibility. The bending portion 23 can bend the distal end constituting portion 22 in a plurality of directions (for example, four directions toward the top, bottom, left, and right) by a knob 25 of the operation portion 18 by a known mechanism.

As shown in FIG. 1, the endoscope 12 has an illumination optical system, an observation optical system, and a treatment instrument insertion channel 26. In addition, the endoscope has an air/water supply mechanism and a suction mechanism. The air/water supply mechanism has a nozzle at a distal end thereof, and is operated by a first button 27 of the operation portion 18. The suction mechanism is in communication with the treatment instrument insertion channel 26, and is operated by a second button 28 of the operation portion 18.

The illumination optical system and the observation optical system are inserted into the distal end constituting portion 22, the bending portion 23, and the tube portion 24 of the insertion portion 17, the operation portion 18, and the universal cord 21 of the endoscope 12. The illumination optical system has an illumination window at the distal end constituting portion 22. The observation optical system has an observation window at the distal end constituting portion.

A distal end of the treatment instrument insertion channel 26 is opened in the distal end constituting portion 22, and a proximal end of the treatment instrument insertion channel 26 is opened in the vicinity of a proximal end portion of the tube portion 24 or the operation portion 18. For example, it is possible to allow the treatment instrument 13 capable of incising and excising a living tissue of the affected part to pass through the inside of the treatment instrument insertion channel 26. Here, as shown in FIG. 1, a treatment instrument insertion port 31 positioned at the proximal end of the treatment instrument insertion channel 26 is provided in the operation portion 18, and a forcep plug 32 (see FIG. 23) is attachable to and detachable from the treatment instrument insertion port 31. The treatment instrument insertion channel 26 is branched into, for example, a known suction path inside the operation portion 18. The suction path is connected to the second button 28. An aspirate is discharged from an aperture (to be described below) of the distal end of the treatment instrument insertion channel 26 through a mouthpiece, a tube, the suction path, and the universal cord 21 by a pressing operation of the second button 28.

The treatment instrument 13 is a conventional treatment instrument (surgical instrument) passing through the inside of the treatment instrument insertion channel 26 of the endoscope 12. The treatment instrument 13 can approach the affected part and perform an incision and excision on the living tissue of the affected part, in a field of view of the endoscope 12.

Figure 2:
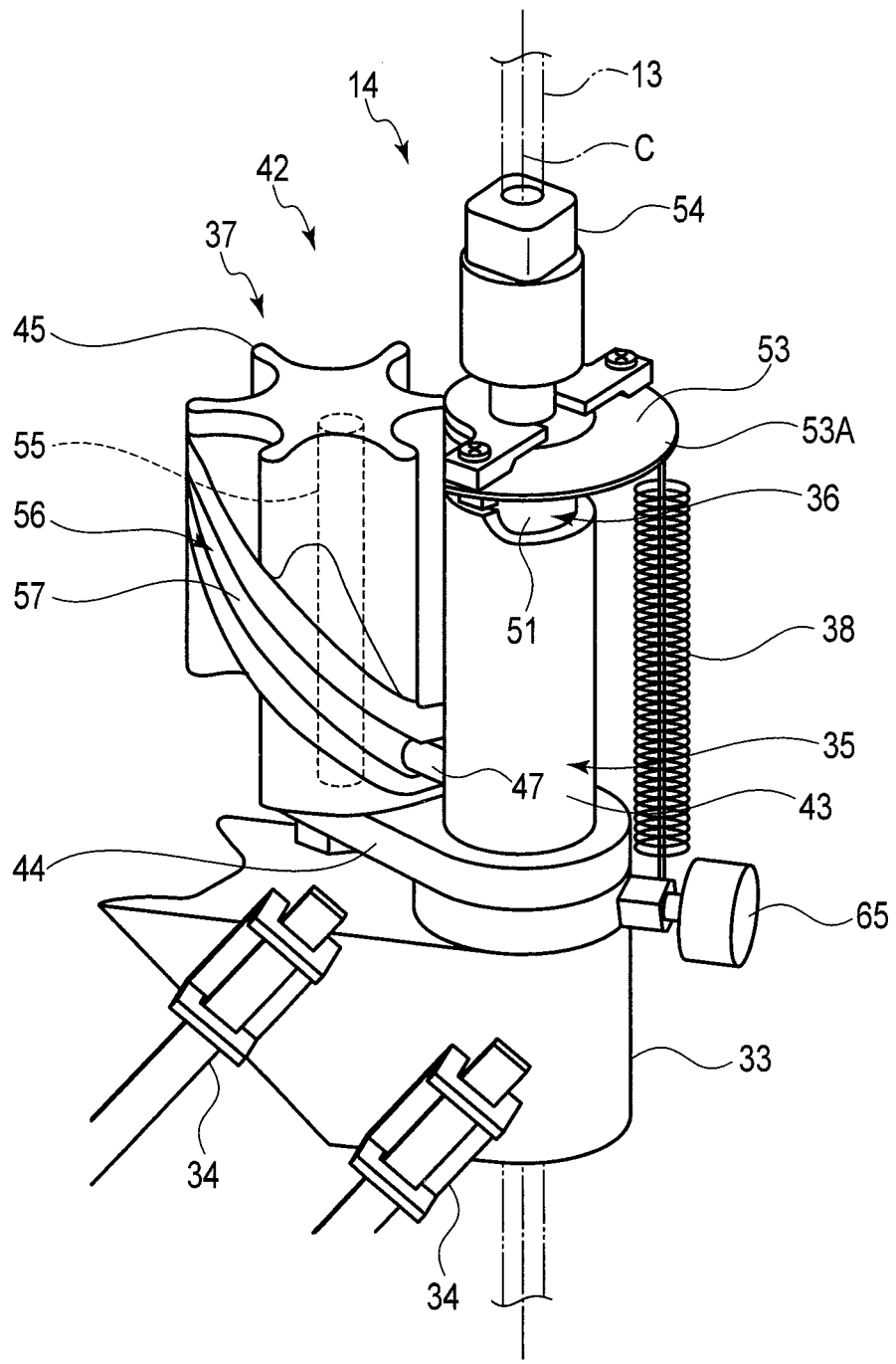
FIG. 2 is a perspective view showing an advance and retreat assisting tool of the endoscope system shown in FIG. 1.
Figure 3:
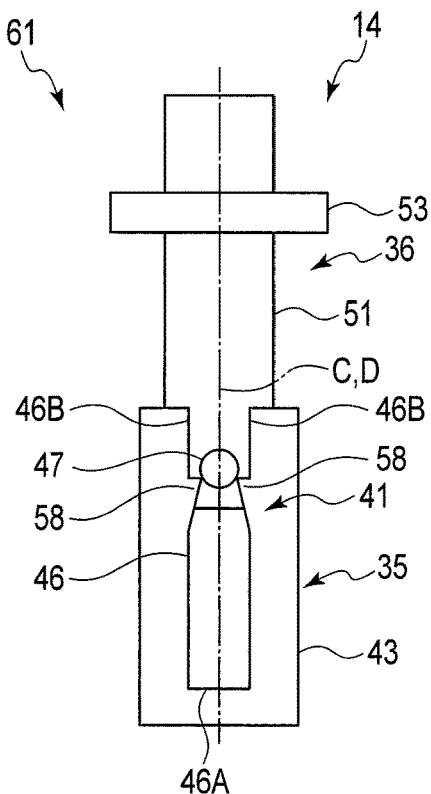
FIG. 3 is a side view of the advance and retreat assisting tool shown in FIG. 2 when viewed from the side in a state where a second cylinder is at a protruding position.

The advance and retreat assisting tool 14 can advance and retreat the treatment instrument 13 passing through the inside of the treatment instrument insertion channel 26 of the endoscope 12 in the direction along the longitudinal direction (direction of a center axis C). As shown in FIGS. 1 to 3, the advance and retreat assisting tool 14 includes a base 33 attached to the operation portion 18, an attaching portion 34 attaching the base 33 to the endoscope 12 such that a through-hole 33A of the base 33 faces the treatment instrument insertion port 31 of the endoscope 12, a first cylinder 35 attached to the base 33, a second cylinder 36 sliding in an advance and retreat direction with respect to the first cylinder 35 along the center axis C of the first cylinder 35, an advance and retreat mechanism 37 advancing and retreating the second cylinder 36 along the center axis C with respect to the first cylinder 35, an assisting portion 38 assisting rotation of the advance and retreat mechanism 37 when the advance and retreat mechanism 37 rotates in one direction, and a positioning portion 41 positioning the second cylinder 36 at a predetermined position with respect to the base 33. The first cylinder 35, the second cylinder 36, the advance and retreat mechanism 37, and the assisting portion 38 constitute a moving unit 42 for advancing and retreating the treatment instrument 13. The attaching portion 34 may be provided at one position or at a plurality of positions. In addition, it is preferable that a shape of the attaching portion 34 is a belt-like shape.

Figure 5:
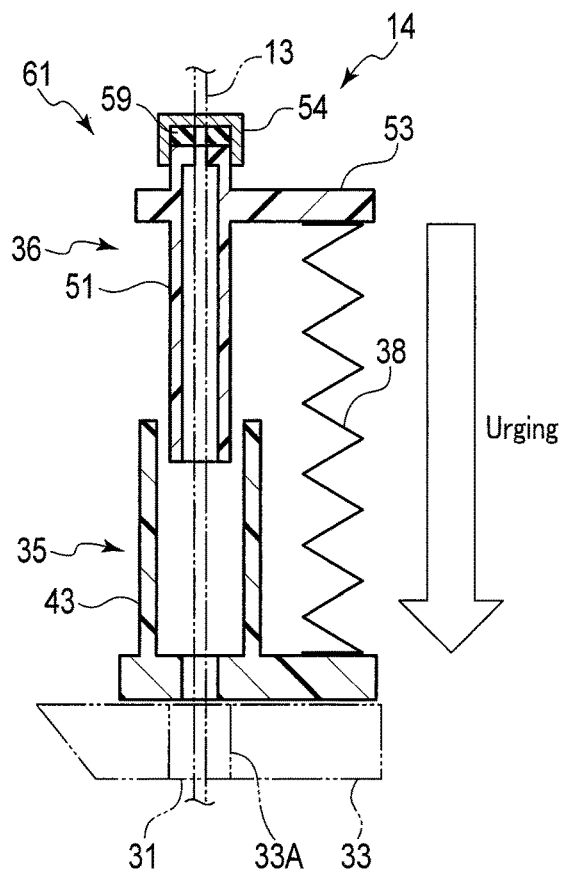
FIG. 5 is a cross-sectional view of the advance and retreat assisting tool shown in FIG. 2, taken in a direction along a center axis of a first cylinder.

The base 33 has the through-hole 33A through which the treatment instrument 13 passes (see FIG. 5). The base 33 can cover, for example, the forcep plug 32 from an upper side (see FIG. 23 and the like).

As shown in FIGS. 2 and 5, the first cylinder 35 is attached to the base 33 such that an inner portion thereof is in communication with the through-hole 33A. The first cylinder 35 has a first main body 43 having a cylindrical shape and a first arm portion 44 extending from a part of the first main body 43 facing the base 33. A dial 45 of the advance and retreat mechanism 37 is rotatably attached to a distal end of the first arm portion 44. The first main body 43 and the first arm portion 44 are molded integrally with each other by, for example, a synthetic resin material. As shown in FIG. 3, the first cylinder 35 has a groove portion 46 extending along an extending direction (the center axis D of the first cylinder 35) of the treatment instrument 13. A pin 47 of the second cylinder 36 to be described below slidably passes through the inside of the groove portion 46. The center axis D of the first cylinder 35 coincides with the center axis C of the treatment instrument 13.

The second cylinder 36 has a second main body 51 having a tubular shape, a holding member 53 protruding from a distal end side opposite to a side of the second main body 51 facing the base 33 in a radial direction of the second main body 51 and having a disk shape, a fixing portion 54 attachable to and detachable from the second main body 51 and having a cap shape, and a fastening portion 59 provided inside the fixing portion 54, compressed when the fixing portion 54 is fastened to the second main body 51 to allow the treatment instrument to be fixed thereto, and having elasticity. The fastening portion 59 is formed in an annular shape by, for example, elastic rubber. The treatment instrument 13 can pass through a hole portion positioned at the center of the fastening portion 59. The fixing portion 54 is fixed to the second main body 51 by, for example, screwing or the like, to elastically deform the fastening portion 59, thereby allowing the fastening portion 59 to be closely adhered to the treatment instrument 13. As a result, the fastening portion 59 engages with the treatment instrument 13, and the treatment instrument 13 and the second cylinder 36 are fixed to each other. In addition, in a state where the fixing portion 54 is fixed to the second main body 51, the fastening portion 59 also functions as a liquid-tight member hindering movement of a liquid between the inside and the outside of the second main body 51 to prevent a body fluid and the like from bleeding to the outside along the treatment instrument 13. The second cylinder 36 can move with respect to the first cylinder 35. A structure fixing the second cylinder 36 and the treatment instrument 13 to each other is not limited thereto. The fixing portion 54 may have a shape having a slit. The treatment instrument 13 may be inserted into the slit of the fixing portion 54, so that the treatment instrument 13 and the second cylinder 36 are integrated with each other by frictional resistance.

As shown in FIGS. 2 and 3, the advance and retreat mechanism 37 includes the dial 45, a rotation shaft 55, and a cam mechanism 56 converting rotation of the dial 45 into advance and retreat of the second cylinder 36 (treatment instrument 13). The dial 45 is provided so as to be rotatable around the rotation shaft 55 provided on the first arm portion 44 of the first cylinder 35. The rotation shaft 55 extends in a direction along the extending direction (direction of the center axis C) of the treatment instrument 13. The cam mechanism 56 includes a cam groove 57 formed in a spiral shape on an outer circumferential surface of the dial 45 and a pin 47 formed in the second cylinder 36 so as to protrude from the second main body 51. For this reason, the dial 45 is rotated by user's fingers, so that the second cylinder 36 can protrude from the first cylinder 35 or the second cylinder 36 can be received in the first cylinder 35, by an action of the cam mechanism 56 (the cam groove 57 and the pin 47). The cam mechanism 56 is an example of a transfer portion converting a rotation force of the dial 45 into a force for advancing and retreating the second cylinder 36 in a direction along the center axis C of the first cylinder 35. Therefore, the advance and retreat mechanism 37 can advance and retreat the treatment instrument 13 by rotating the dial 45 with the user's fingers. That is, when viewed from an opposite side to the base 33, for example, when the dial 45 is rotated counterclockwise, the pin 47 is moved toward the opposite side to the base 33 by an action of the cam groove 57. Likewise, when viewed from the opposite side to the base 33, for example, when the dial 45 is rotated clockwise, the pin 47 is moved toward the base 33 by an action of the cam groove 57.

Figure 4:
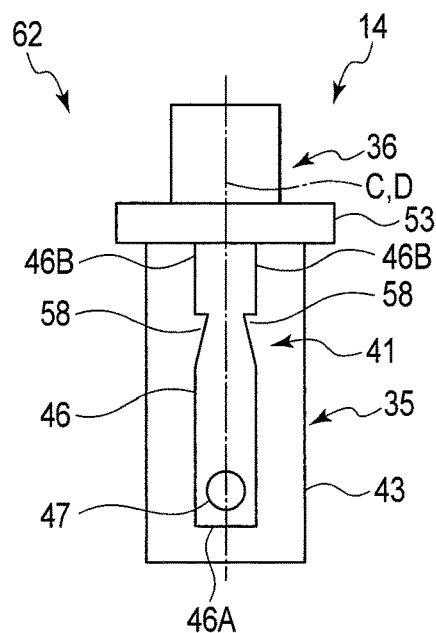
FIG. 4 is a side view of the advance and retreat assisting tool shown in FIG. 2 when viewed from the side in a state where the second cylinder is at a received position.

As shown in FIGS. 3 and 4, the positioning portion 41 includes a pair of convex portions 58 protruding into the groove portion 46 of the first cylinder 35. Each of the convex portions 58 is formed in a "wedge shape" protruding so as to approach the center axis D of the groove as the distance to an end portion 46B on an opposite side to a bottom portion 46A of the groove portion 46 is decreased. As shown in FIG. 3, when the second cylinder 36 moves from a protruding position 61 at which it protrudes from the first cylinder 35 to a received position 62 at which it is received in the first cylinder 35, the pin 47 has a structure in which it is caught by the convex portions 58. Therefore, a large resistance force is generated when the pin 47 passes between the convex portions 58. As a result, the positioning portion 41 prevents the second cylinder 36 from being moved from the protruding position 61 to the received position 62 when the user does not intend this movement. For this reason, it is difficult for the second cylinder 36 to move from the protruding position 61 to the received position 62, but since a restoring force of a tension spring of the assisting portion 38 acts on the movement of the second cylinder 36 in this direction, there is no hindrance to an advance and retreat operation of the treatment instrument 13.

On the other hand, as shown in FIGS. 3 and 4, when the second cylinder 36 moves from the received position 62 at which it is received in the first cylinder 35 to the protruding position 61 at which it protrudes from the first cylinder 35, the positioning portion 41 described above has the "wedge shape", so that it is difficult for the pin 47 to be caught by the convex portions 58. Therefore, a large resistance force is not generated when the pin 47 passes between the convex portions 58. For this reason, since the resistance force at the time of the movement is smaller than that when the second cylinder 36 moves from the protruding position 61 to the received position 62, a load applied to the user's fingers when moving the second cylinder 36 from the received position 62 to the protruding position 61 is reduced. On the other hand, since a predetermined frictional force acts when the pin 47 passes between the convex portions 58, the positioning portion 41 prevents the second cylinder 36 from being moved from the received position 62 to the protruding position 61 when the user does not intend this movement.

As shown in FIG. 2, the assisting portion 38 is formed of a member having elasticity, for example, a tension spring (preferably, a tension coil spring) spanned between the base 33 and the holding member 53 of the second cylinder 36. An end portion of the assisting portion 38 adjacent to the base 33 is fixed to the base 33 through a fixing member 65 (screw) fixed to the base 33. An end portion of the assisting portion 38 on the opposite side to the base 33 is fixed to the base 33 through the holding member 53 (a locking hole 53A formed in the holding member 53) fixed to the second cylinder 36 and having the disk shape. The assisting portion 38 may be spanned between the first cylinder 35 and the second cylinder 36. The assisting portion 38 is disposed outside the first cylinder 35.

Figure 6:
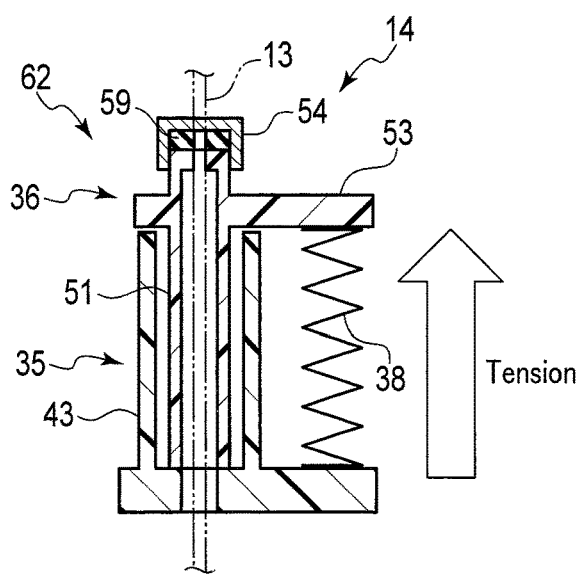
FIG. 6 is a side view of the advance and retreat assisting tool shown in FIG. 2 when viewed from the side.
Figure 7:
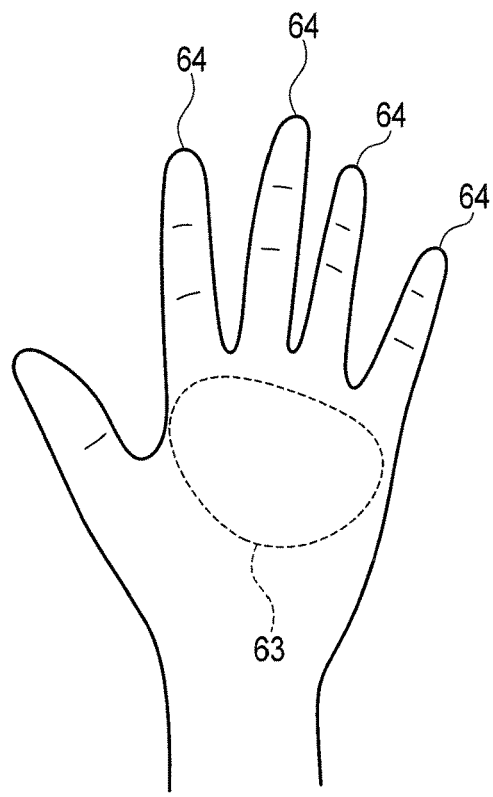
FIG. 7 is a front view showing a position relationship between fingers and a palm surface (palm) of a left hand.

Next, an effect of the present embodiment will be described with reference to FIGS. 5 to 7 and the like.

The endoscope 12 according to the present embodiment is designed such that the operation portion 18 is grasped with the left hand and the insertion portion 17 is grasped with the right hand, as shown in FIG. 1. As shown in FIG. 1, the treatment instrument 13 passes through the treatment instrument insertion channel 26 of the endoscope 12. In a state where the operation portion 18 is grasped with the left hand as described above, for example, when the user wants to further protrude the treatment instrument 13 from the endoscope 12 to advance the treatment instrument 13, the user moves fingers 64 in a direction in which the fingers 64 become distant from a palm surface 63 to rotate the dial 45 in a clockwise direction when viewed from the opposite side to the base 33. As a result, the pin 47 and the second cylinder 36 are moved toward the treatment instrument insertion port 31 (base 33) by an action of the cam groove 57. In this case, as shown in FIG. 5, the restoring force of the tension spring of the assisting portion 38 acts to urge the second cylinder 36 toward the base 33, thereby assisting the movement of the second cylinder 36. Therefore, a force for rotating the dial 45 in the clockwise direction is reduced. As a result, even in a case where the user moves the fingers 64 in the direction in which the fingers 64 becomes distant from the palm surface 63, which is a direction in which it is ergonomically difficult to apply the force, the rotation of the dial 45 and the advance of the treatment instrument 13 are assisted by an action of the assisting portion 38. An urging force of the tension spring of the assisting portion 38 is smaller than a resistance force (frictional force) when the second cylinder 36 slides with respect to the first cylinder 35. In this case, the resistance force when the second cylinder 36 slides includes at least one of a frictional force between the first cylinder 35 and the second cylinder 36 and a frictional force applied when the advance and retreat mechanism (dial) advances or retreats the second cylinder 36.

On the other hand, when the user wants to retreat the treatment instrument 13 so as to return the treatment instrument 13 toward the endoscope 12, the user moves the fingers 64 in a direction in which the fingers 64 approach the palm surface 63 to rotate the dial 45 in a counterclockwise direction when viewed from the opposite side to the base 33. As a result, the pin 47 and the second cylinder 36 are moved toward an opposite side (protruding position 61) to the treatment instrument insertion port 31 by an action of the cam groove 57. In this case, as shown in FIG. 6, the restoring force of the tension spring of the assisting portion 38 becomes resistance when moving the second cylinder 36. However, since an operation of moving the fingers 64 in the direction in which the fingers 64 approach the palm surface 63 is an operation in which it is ergonomically easy to apply a force, the rotation of the dial 45 in the counterclockwise direction (retreat of the treatment instrument 13) is hardly hindered. In this example, the movement between the protruding position 61 and the received position 62 has been described by way of example, but the same effect is also achieved in the movement at an intermediate position between the protruding position 61 and the received position 62.

According to the first embodiment, the advance and retreat assisting tool 14 for a treatment instrument can be configured as follows. The advance and retreat assisting tool 14 for a treatment instrument includes the base 33 which has the through-hole 33A, the attaching portion 34 which attaches the base 33 to the endoscope 12 such that the through-hole 33A faces the treatment instrument insertion port 31 of the endoscope 12, the first cylinder 35 which is attached to the base 33 such that the inner portion thereof is in communication with the through-hole 33A, the second cylinder 36 which has the fixing portion 54 fixing the treatment instrument 13 inserted into the treatment instrument insertion port 31 and slides in the advance and retreat direction with respect to the first cylinder 35 along the center axis C of the first cylinder 35, the advance and retreat mechanism 37 which advances and retreats the second cylinder 36 along the center axis C with respect to the first cylinder 35 by rotation, and the assisting portion 38 which urges the second cylinder 36 in a predetermined direction along the center axis C with respect to the base 33 with the urging force smaller than the resistance force when the second cylinder 36 slides and assists the rotation of the advance and retreat mechanism 37 when the advance and retreat mechanism 37 rotates in one direction.

According to such a configuration, it is possible to easily perform the rotation of the advance and retreat mechanism 37 in one direction, so that the force required for the operation of the advance and retreat mechanism 37 is reduced, and it is thus possible to provide the advance and retreat assisting tool 14 for a treatment instrument in which operability is improved. In addition, since the assisting portion 38 urges the second cylinder 36 with the urging force smaller than the resistance force when the second cylinder 36 slides, it is possible to prevent a position of the treatment instrument 13 from being moved by the urging force of the assisting portion 38 when the user does not intend this movement.

The advance and retreat assisting tool for a treatment instrument 13 includes the positioning portion 41 which positions the urged second cylinder 36 at a predetermined position with respect to the base 33. According to such a configuration, due to the positioning portion 41, it is possible to prevent the second cylinder 36 from being moved when the user does not intend this movement. Therefore, it is possible to suppress the treatment instrument 13 from being freely moved, so that is possible to prevent a defect such as deviation of the treatment instrument 13 from the field of view of the endoscope 12.

The positioning portion 41 defines a relative positional relationship between the first cylinder 35 and the second cylinder 36 in the direction of the center axis C. According to such a configuration, it is possible to determine the relative positional relationship between the first cylinder 35 and the second cylinder 36 by the positioning portion 41, such that it is possible to prevent the defect such as the deviation of the treatment instrument 13 from the field of view of the endoscope 12 without the treatment instrument 13 being freely moved against intension of the user.

An outer diameter of the second cylinder 36 is smaller than an inner diameter of the first cylinder 35, and the second cylinder 36 advances and retreats between a position in a state where it is inserted into the first cylinder 35 and a position in a state where it protrudes from the first cylinder 35. According to such a configuration, it is possible to realize a configuration in which the second cylinder 36 moves with respect to the first cylinder 35 with a simple structure.

The advance and retreat mechanism 37 includes the dial 45 which rotates around the predetermined rotation shaft 55 by a force operated from the outside and the transfer portion which converts the rotation force of the dial 45 into the force for advancing and retreating the second cylinder 36 in the direction along the axis. According to such a configuration, it is possible to advance and retreat the treatment instrument 13 by a simple structure through the dial 45 and the transfer portion, so that it is possible to reduce a manufacturing cost by a reduction in the number of components.

In addition, according to the first embodiment, the advance and retreat assisting tool 14 for a treatment instrument can be configured as follows. The advance and retreat assisting tool 14 for a treatment instrument includes the first cylinder 35, the second cylinder 36 which has the fixing portion 54 fixing the treatment instrument 13 inserted into the endoscope 12 and slides in an extending direction of the first cylinder 35 with respect to the first cylinder 35, the advance and retreat mechanism 37 which causes the second cylinder 36 to slide in the extending direction of the first cylinder 35 by the rotation, and the assisting portion 38 which assists the rotation of the advance and retreat mechanism 37 when the advance and retreat mechanism 37 is rotated by moving the fingers 64 in the direction in which the fingers 64 become distant from the palm surface 63. According to such a configuration, when the fingers 64 move in the direction in which it is ergonomically difficult to apply the force, it is possible to assist the rotation of the advance and retreat mechanism 37 by the assisting portion 38. According to such a configuration, it is possible to realize the advance and retreat assisting tool 14 for a treatment instrument in which user's operability is improved.

In modified examples to be described below, parts different from those of the above embodiment will be mainly described, and illustration or description of parts common to those of the above embodiment will be omitted.

First Modified Example

Figure 8:
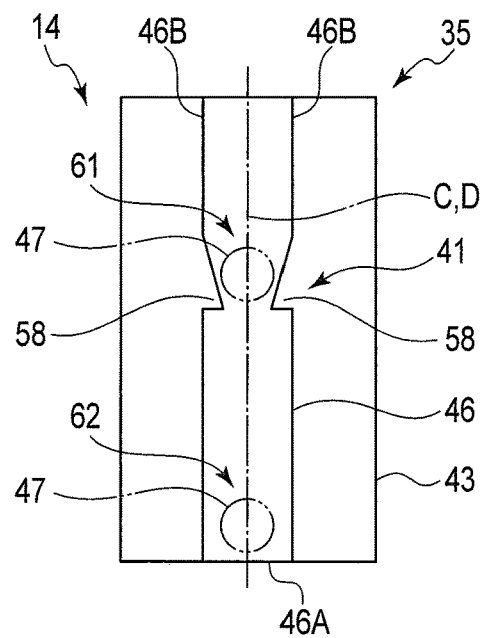
FIG. 8 is a side view schematically showing a positioning portion of an advance and retreat assisting tool of an endoscope system according to a first modified example.

FIG. 8 shows a positioning portion 41 of an endoscope system 11 according to a first modified example. In the present modified example, a structure of the positioning portion 41 is different from that of the above embodiment.

As shown in FIG. 8, the positioning portion 41 includes a pair of convex portions 58 protruding into the groove portion 46 of the first cylinder 35. Each of the convex portions 58 is formed in a "wedge shape" protruding so as to approach the center axis D of the groove as the distance to the bottom portion 46A of the groove portion 46 is decreased. That is, in the first modified example, a direction of a tip of the wedge shape of the convex portion 58 is an opposite direction.

An operation of the endoscope system according to the first modified example will be described.

As shown in FIG. 8, when the second cylinder 36 (see FIG. 3) moves from the protruding position 61 at which it protrudes from the first cylinder 35 to the received position 62 at which it is received in the first cylinder 35, the positioning portion 41 described above has the "wedge shape", so that it is difficult for the pin 47 to be caught by the convex portions 58. Therefore, a large resistance force is not generated when the pin 47 passes between the convex portions 58. On the other hand, since a predetermined frictional force acts when the pin 47 passes between the convex portions 58, the positioning portion 41 prevents the second cylinder 36 from being moved from the protruding position 61 to the received position 62 when the user does not intend this movement. In addition, as the second cylinder 36 moves from the protruding position 61 to the received position 62, the restoring force of the tension spring of the assisting portion 38 acts. Therefore, a load applied to the user's fingers when moving the second cylinder 36 from the protruding position 61 to the received position 62 is reduced.

On the other hand, when the second cylinder 36 moves from the received position 62 at which it is received in the first cylinder 35 to the protruding position 61, a large resistance force is generated when moving the second cylinder 36. For this reason, it is possible to prevent the second cylinder 36 from being moved from the received position 62 to the protruding position 61 when the user does not intend this movement. In this case, the movement of the second cylinder 36 from the received position 62 to the protruding position 61 corresponds to an operation of moving the fingers in the direction in which the fingers approach the palm surface 63 to rotate the dial 45. For this reason, the rotation of the dial 45 in this direction is an operation in which it is ergonomically easy to apply a force, so that an advance and retreat operation of the treatment instrument 13 is not hindered.

Second Modified Example

Figure 9:
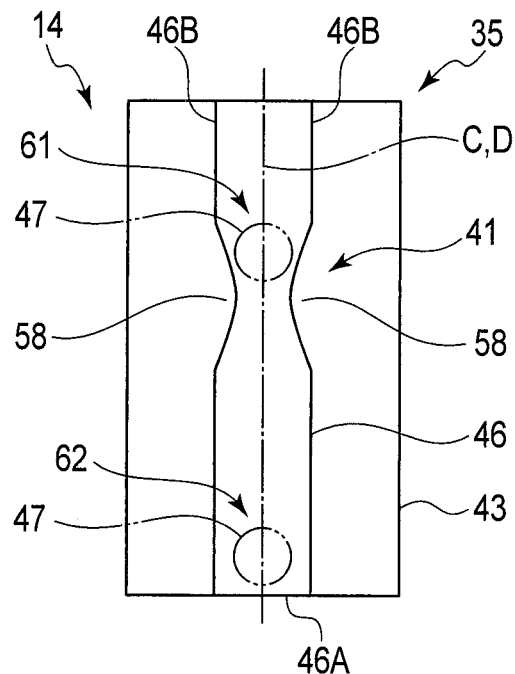
FIG. 9 is a side view schematically showing a positioning portion of an advance and retreat assisting tool of an endoscope system according to a second modified example.

FIG. 9 shows a positioning portion 41 of an endoscope system 11 according to a second modified example. In the present modified example, a structure of the positioning portion 41 is different from those of the above embodiment and the above modified example.

As shown in FIG. 9, the positioning portion 41 includes a pair of convex portions 58 protruding into the groove portion 46 of the first cylinder 35. Each of the convex portions 58 is formed in, for example, a "mountain shape of a normal distribution" or "bell shape".

An operation of the endoscope system according to the second modified example will be described.

When the second cylinder 36 (see FIG. 3) moves from the protruding position 61 at which it protrudes from the first cylinder 35 to the received position 62 at which it is received in the first cylinder 35, a predetermined frictional force acts when the pin 47 passes between the convex portions 58. For this reason, the positioning portion 41 prevents the second cylinder 36 from being moved from the protruding position 61 to the received position 62 when the user does not intend this movement. As the second cylinder 36 moves from the protruding position 61 to the received position 62, the restoring force of the tension spring of the assisting portion 38 acts. For this reason, since the resistance force at the time of the movement is smaller than that when the second cylinder 36 moves from the received position 62 to the protruding position 61, a load applied to the user's fingers when moving the second cylinder 36 from the protruding position 61 to the received position 62 is reduced.

On the other hand, when the second cylinder 36 moves from the received position 62 at which it is received in the first cylinder 35 to the protruding position 61, the same resistance force as that when the second cylinder 36 moves from the protruding position 61 to the received position 62 is generated. For this reason, it is possible to prevent the second cylinder 36 from being moved from the received position 62 to the protruding position 61 when the user does not intend this movement. In this case, the movement of the second cylinder 36 from the received position 62 to the protruding position 61 corresponds to an operation of moving the fingers in the direction in which the fingers approach the palm surface 63 to rotate the dial 45. For this reason, the rotation of the dial 45 in this direction is an operation in which it is ergonomically easy to apply a force, so that an advance and retreat operation of the treatment instrument 13 is not hindered.

Third Modified Example

Figure 10:
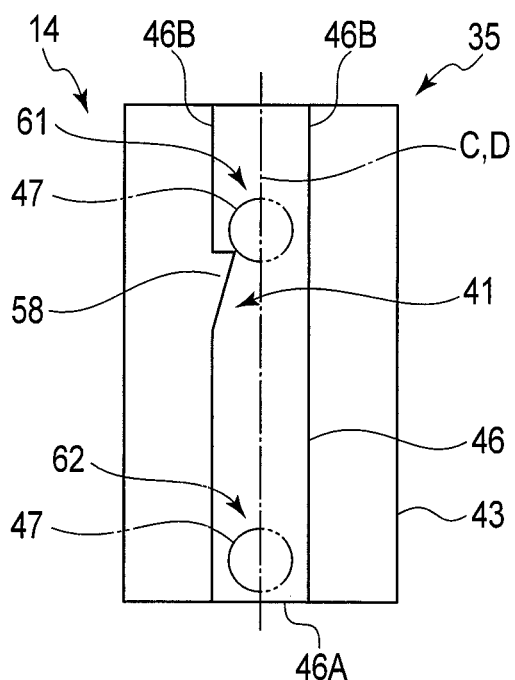
FIG. 10 is a side view schematically showing a positioning portion of an advance and retreat assisting tool of an endoscope system according to a third modified example.

FIG. 10 shows a positioning portion 41 of an endoscope system 11 according to a third modified example. In the present modified example, a structure of the positioning portion 41 is different from those of the above embodiment and the above modified examples.

As shown in FIG. 10, the positioning portion 41 includes one convex portion 58 protruding into the groove portion 46 of the first cylinder 35. The convex portion 58 has the same shape as that in the above embodiment, and is formed in a "wedge shape" protruding so as to approach the center axis D of the groove as the distance to the end portion 46B on the opposite side to the bottom portion 46A of the groove portion 46 is decreased.

An operation of the endoscope system 11 according to the third modified example will be described.

As shown in FIG. 10, when the second cylinder 36 (see FIG. 3) moves from the protruding position 61 at which it protrudes from the first cylinder 35 to the received position 62 at which it is received in the first cylinder 35, the pin 47 has a structure in which it is caught by the convex portions 58. Therefore, a large resistance force is generated when the pin 47 passes between the convex portions 58. As a result, the positioning portion 41 prevents the second cylinder 36 from being moved from the protruding position 61 to the received position 62 when the user does not intend this movement. For this reason, it is difficult for the second cylinder 36 to move from the protruding position 61 to the received position 62, but since a restoring force of a tension spring of the assisting portion 38 acts on the movement of the second cylinder 36 in this direction, there is no hindrance to an advance and retreat operation of the treatment instrument 13.

On the other hand, when the second cylinder 36 moves from the received position 62 at which it is received in the first cylinder 35 to the protruding position 62 at which it protrudes from the first cylinder 35, the positioning portion 41 described above has the "wedge shape", so that it is difficult for the pin 47 to be caught by the convex portions 58. Therefore, a large resistance force is not generated when the pin 47 passes between the convex portions 58. For this reason, since the resistance force at the time of the movement is smaller than that when the second cylinder 36 moves from the protruding position 61 to the received position 62, a load applied to the user's fingers when moving the second cylinder 36 from the received position 62 to the protruding position 61 is reduced. On the other hand, since a predetermined frictional force acts when the pin 47 passes through the convex portion 58, the positioning portion 41 prevents the second cylinder 36 from being moved from the received position 62 to the protruding position 61 when the user does not intend this movement.

Fourth Modified Example

Figure 11:
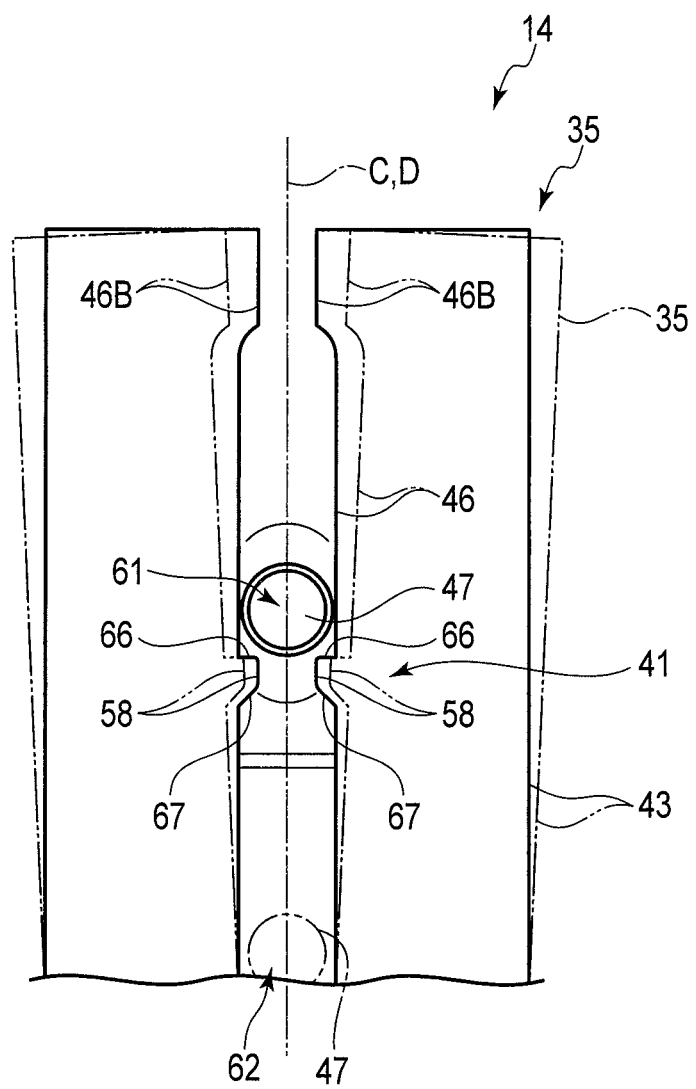
FIG. 11 is a side view schematically showing a positioning portion of an advance and retreat assisting tool of an endoscope system according to a fourth modified example.

FIG. 11 shows a positioning portion 41 of an endoscope system 11 according to a fourth modified example. In the present modified example, a structure of the positioning portion 41 is different from those of the above embodiment and the above modified examples.

As shown in FIG. 11, the positioning portion 41 includes a pair of convex portions 58 protruding into the groove portion 46 of the first cylinder 35. Each of the convex portions 58 is formed in, for example, a trapezoidal shape. One leg (first leg 66) of the trapezoidal shape of the convex portion 58 is orthogonal to the center axis C (a moving direction of the pin 47 or the center axis D of the groove) of the first cylinder 35, and the other leg (second leg 67) of the trapezoidal shape of the convex portion 58 is oblique with respect to the center axis C (the moving direction of the pin 47 or the center axis D of the groove) of the first cylinder 35.

The groove portion 46 has a shape (slotted shape) in which an opening portion is in communication with the outside. The first cylinder 35 may have a plurality of slits extending in the direction of the center axis C of the first cylinder 35, in addition to the groove portion 46. In addition to the groove portion 46, one slit is provided or a plurality of slits are provided, so that rigidity of the first main body 43 of the first cylinder 35 is reduced, and the first cylinder 35 is easily elastically deformed in the vicinity of the positioning portion 41.

An operation of the endoscope system 11 according to the fourth modified example will be described.

When the second cylinder 36 (see FIG. 3) moves from the protruding position 61 at which it protrudes from the first cylinder 35 to the received position 62 at which it is received in the first cylinder 35, the pin 47 abuts on the convex portions 58 (the first legs 66) of the positioning portion 41 to pass between the convex portions 58 while elastically deforming a part of the first main body 43 of the first cylinder 35 as represented by a two-dot chain line in FIG. 11. In this case, since the moving direction of the pin 47 and a direction of the first leg 66 are perpendicular to each other, a force required for elastically deforming the first main body 43 of the first cylinder 35 is relatively large. Since a resistance force is generated by a reaction of the force for elastically deforming the first main body 43 as described above, the second cylinder 36 is prevented from being moved from the protruding position 61 to the received position 62 when the user does not intend this movement. In this case, it becomes difficult for the second cylinder 36 to move from the protruding position 61 to the received position 62, but as the second cylinder 36 moves from the protruding position 61 to the received position 62, the restoring force of the tension spring of the assisting portion 38 acts. For this reason, since the resistance force at the time of the movement is smaller than that when the second cylinder 36 moves from the received position 62 to the protruding position 61, a load applied to the user's fingers when moving the second cylinder 36 from the protruding position 61 to the received position 62 is reduced.

On the other hand, when the second cylinder 36 moves from the received position 62 at which it is received in the first cylinder 35 to the protruding position 61, the pin 47 abuts on the convex portions 58 (the second legs 67) of the positioning portion 41 to pass between the convex portions 58 while elastically deforming a part of the first main body 43 of the first cylinder 35. In this case, since the moving direction of the pin 47 and a direction of the second leg 67 are oblique with respect to each other, the force necessary for elastically deforming the first main body 43 of the first cylinder 35 is smaller than that when the second cylinder 36 moves from the protruding position 61 to the received position 62. However, even in such a case, a slight force is required for elastically deforming the first main body 43, so that the second cylinder 36 is prevented from being moved from the received position 62 to the protruding position 61 when the user does not intend this movement. In this case, the movement of the second cylinder 36 from the received position 62 to the protruding position 61 corresponds to an operation of moving the fingers in the direction in which the fingers approach the palm surface 63 to rotate the dial 45. For this reason, the rotation of the dial 45 in this direction is an operation in which it is ergonomically easy to apply a force, so that an advance and retreat operation of the treatment instrument 13 is not hindered.

Fifth Modified Example

An endoscope system 11 according to a fifth modified example will be described with reference to FIGS. 12 and 13. In the present modified example, structures of an advance and retreat mechanism 37 and an assisting portion 38 are different from those of the above embodiment and the above modified examples.

The advance and retreat mechanism 37 includes a dial 45 and a cam mechanism 56 (transfer portion) converting rotation of the dial 45 into advance and retreat of the second cylinder 36 (treatment instrument 13). The dial 45 is provided so as to be rotatable around the rotation shaft 55 provided on the first arm portion 44 of the first cylinder 35. The cam mechanism 56 includes a cam groove 57 formed in a spiral shape on an outer circumferential surface of the dial 45 and a pin 47 formed in the second cylinder 36 so as to protrude from the second main body 51. In the present modified example, the cam groove 57 is formed in a spiral shape in an opposite direction to that of the above embodiment. For this reason, when viewed from the opposite side to the base 33, when the dial 45 is rotated clockwise, the pin 47 is moved toward the opposite side to the base 33 by an action of the cam groove 57. When viewed from the opposite side to the base 33, when the dial 45 is rotated counterclockwise, the pin 47 is moved toward the base 33 by an action of the cam groove 57.

The assisting portion 38 is formed of a compression spring (compression coil spring) spanned between the first cylinder 35 and the holding member 53 of the second cylinder 36. The assisting portion 38 may be spanned between the base 33 and the second cylinder 36 as in the above embodiment.

An effect of the present modified example will be described with reference to FIGS. 12 and 13.

When the user wants to advance the treatment instrument 13 by further protruding the treatment instrument 13 from the endoscope 12, the user moves the fingers 64 in the direction in which the fingers 64 approach the palm surface 63 to rotate the dial 45 in the counterclockwise direction when viewed from the opposite side to the base 33. As a result, the pin 47 and the second cylinder 36 are moved toward the treatment instrument insertion port 31 (received position 62) by an action of the cam groove 57. In this case, as shown in FIG. 12, a force acts so as to compress the compression spring of the assisting portion 38, and a force acting as a reaction to the force thus becomes a resistance force when moving the second cylinder 36. However, since an operation of moving the fingers 64 in the direction in which the fingers 64 approach the palm surface 63 is an operation in which it is ergonomically easy to apply a force, the rotation of the dial 45 in the counterclockwise direction (advance of the treatment instrument 13) is hardly hindered.

On the other hand, when the user wants to retreat the treatment instrument 13 so as to return the treatment instrument 13 toward the endoscope 12, the user moves the fingers in the direction in which the fingers becomes distant from the palm surface 63 to rotate the dial 45 in the clockwise direction when viewed from the opposite side to the base 33. As a result, the pin 47 and the second cylinder 36 are moved toward the opposite side (protruding position 61) to the treatment instrument insertion port 31 by an action of the cam groove 57. In this case, as shown in FIG. 12, a restoring force of the compression spring of the assisting portion 38 acts to assist the movement of the second cylinder 36, and a force for rotating the dial 45 in the clockwise direction is thus reduced. As a result, even in a case where the user moves the fingers in the direction in which it is ergonomically difficult to apply the force, the rotation of the dial 45 and the advance of the treatment instrument 13 are assisted by an action of the assisting portion 38. In this example, the movement between the protruding position 61 and the received position 62 has been described by way of example, but the same effect is also achieved in the movement at an intermediate position between the protruding position 61 and the received position 62.

Sixth Modified Example

An endoscope system 11 according to a sixth modified example will be described with reference to FIGS. 14 and 15. In the present modified example, a position at which an assisting portion 38 is installed is different from those of the above embodiment and the above modified examples.

The assisting portion 38 is formed of a tension spring (tension coil spring) spanned between the first cylinder 35 and the second cylinder 36. The assisting portion 38 is disposed inside the first cylinder 35.

An effect of the present modified example will be described with reference to FIGS. 14 and 15.

When the user wants to advance the treatment instrument 13 by further protruding the treatment instrument 13 from the endoscope 12, the user moves the fingers 64 in the direction in which the fingers 64 become distant from the palm surface 63 to rotate the dial 45 in the clockwise direction when viewed from a distal end side opposite to the first arm portion 44 of the rotation shaft 55. As a result, the pin 47 and the second cylinder 36 are moved toward the treatment instrument insertion port 31 (base 33) by an action of the cam groove 57. In this case, as shown in FIG. 14, the restoring force of the tension spring of the assisting portion 38 acts to urge the second cylinder 36 toward the base 33, thereby assisting the movement of the second cylinder 36. Therefore, a force for rotating the dial 45 in the clockwise direction is reduced. As a result, even in a case where the user moves the fingers in the direction in which it is ergonomically difficult to apply the force, the rotation of the dial 45 and the advance of the treatment instrument 13 are assisted by an action of the assisting portion 38.

On the other hand, when the user wants to retreat the treatment instrument 13 so as to return the treatment instrument 13 toward the endoscope 12, the user moves the fingers in the direction in which the fingers approach the palm surface 63 to rotate the dial 45 in the counterclockwise direction when viewed from a distal end side of the rotation shaft 55. As a result, the pin 47 and the second cylinder 36 are moved toward the opposite side to the treatment instrument insertion port 31 by an action of the cam groove 57. In this case, as shown in FIG. 15, the restoring force of the tension spring of the assisting portion 38 becomes a resistance of the movement of the second cylinder 36. However, since an operation of moving the fingers in the direction in which the fingers approach the palm surface 63 is an operation in which it is ergonomically easy to apply a force, the rotation of the dial 45 in the counterclockwise direction (retreat of the treatment instrument 13) is hardly hindered. In this example, the movement between the protruding position 61 and the received position 62 has been described by way of example, but the same effect is also achieved in the movement at an intermediate position between the protruding position 61 and the received position 62.

Seventh Modified Example

An endoscope system 11 according to a seventh modified example will be described with reference to FIGS. 16 and 17. In the present modified example, a structure of a positioning portion 41 is different from those of the above embodiment and the above modified example.

Figure 16:
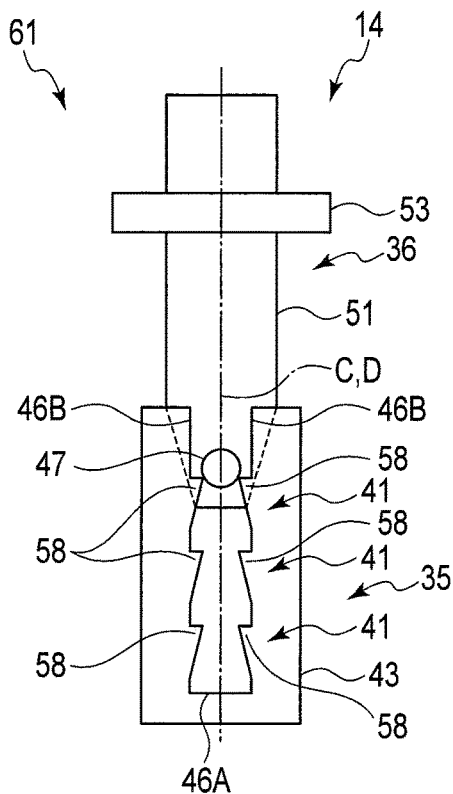
FIG. 16 is a side view schematically showing a positioning portion of an advance and retreat assisting tool of an endoscope system according to a seventh modified example in a state where a second cylinder is at a protruding position.
Figure 17:
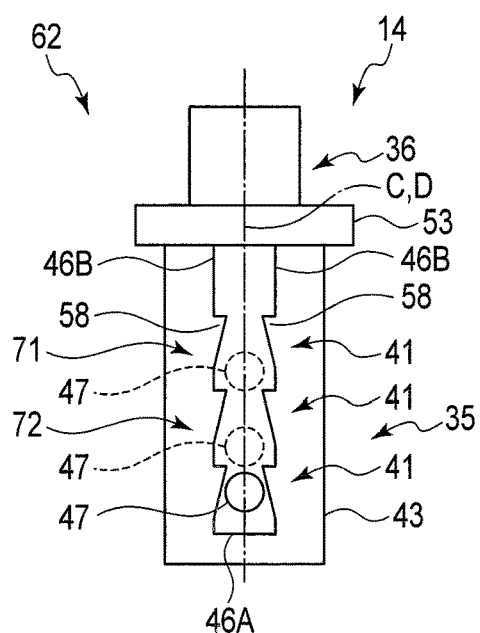
FIG. 17 is a side view schematically showing the positioning portion of the advance and retreat assisting tool of the endoscope system according to the seventh modified example in a state where the second cylinder is at a received position.

As shown in FIG. 16, the positioning portion 41 is distributed and provided at a plurality of positions along the direction of the center axis C of the first cylinder 35 in the groove of the first cylinder 35. That is, the positioning portion 41 has a plurality of sets of convex portions 58 distributed and disposed along the direction of the center axis C of the first cylinder 35. The respective convex portions 58 are provided to face each other in the groove 46.

Each of the convex portions 58 is formed in a "wedge shape" protruding so as to approach the center axis D of the groove as the distance to the end portion 46B on the opposite side to the bottom portion 46A of the groove portion 46 is decreased. As shown in FIG. 16, when the second cylinder 36 moves from the protruding position 61 to the received position 62, the pin 47 has a structure in which it is caught by the convex portions 58. Therefore, a large resistance force is generated when the pin 47 passes between the convex portions 58. On the other hand, as shown in FIG. 17, when the second cylinder 36 moves from the received position 62 to the protruding position 61, although a predetermined resistance force is applied to the pin 47 when the pin 47 passes between the convex portions 58, the second cylinder 36 can be moved with a relatively small force.

In the present modified example, a plurality of intermediate positions are defined between the protruding position 61 at which the second cylinder 36 protrudes from the first cylinder 35 and the received position 62 at which the second cylinder 36 is received in the first cylinder 35. In the present modified example, two intermediate positions are provided. A first intermediate position 71 is set to a position close to the protruding position 61, and this position is defined by a second convex portion 58 from the end portion 46B of the groove 46 and the pin 47. A second intermediate position 72 is set to a position close to the received position 62, and this position is defined by a second convex portion 58 from the bottom portion 46A of the groove 46 and the pin 47. It should be noted that two or more intermediate positions may be set.

An effect of the present modified example will be described with reference to FIGS. 16 and 17.

When the user wants to advance the treatment instrument 13 or wants to retreat the treatment instrument 13, the user can advance or retreat the treatment instrument 13 by rotating the dial 45 in the clockwise direction or the counterclockwise direction when viewed from the opposite side of the base 33, as in the above embodiment. In the present modified example, further, the user can not only fixedly hold the pin 47 and the second cylinder 36 at the protruding position 61 and the received position 62 by the positioning portion 41, but also fixedly hold the pin 47 and the second cylinder 36 at the intermediate positions (the first intermediate position 71 and the second intermediate position 72) between the protruding position 61 and the received position 62 by the positioning portion 41.

According to the present modified example, the positioning portion 41 is provided between the first cylinder 35 and the second cylinder 36, and defines a relative positional relationship between the first cylinder 35 and the second cylinder 36 in the direction of the center axis C in a plurality of steps. According to such a configuration, for example, the following treatment can be performed. For example, under view of the endoscope 12, when, for example, the innermost part is treated in a hole of a medical examinee (subject), the treatment instrument 13 can be held at the most advanced position. In addition, when a front side is treated in the hole of the medical examinee, the treatment instrument 13 can be held at the most retreated position. Further, when an intermediate position between the innermost part and the front side is treated in the hole of the medical examinee, the treatment instrument 13 is held at the intermediate position between the innermost part and the front side. As described above, the endoscope system according to present modified example is particularly useful, for example, when the user wants to change a position of the treatment instrument 13 stepwise in the direction of the center axis C depending on a position at which the treatment is performed with the treatment instrument 13.

Eighth Modified Example

Figure 18:
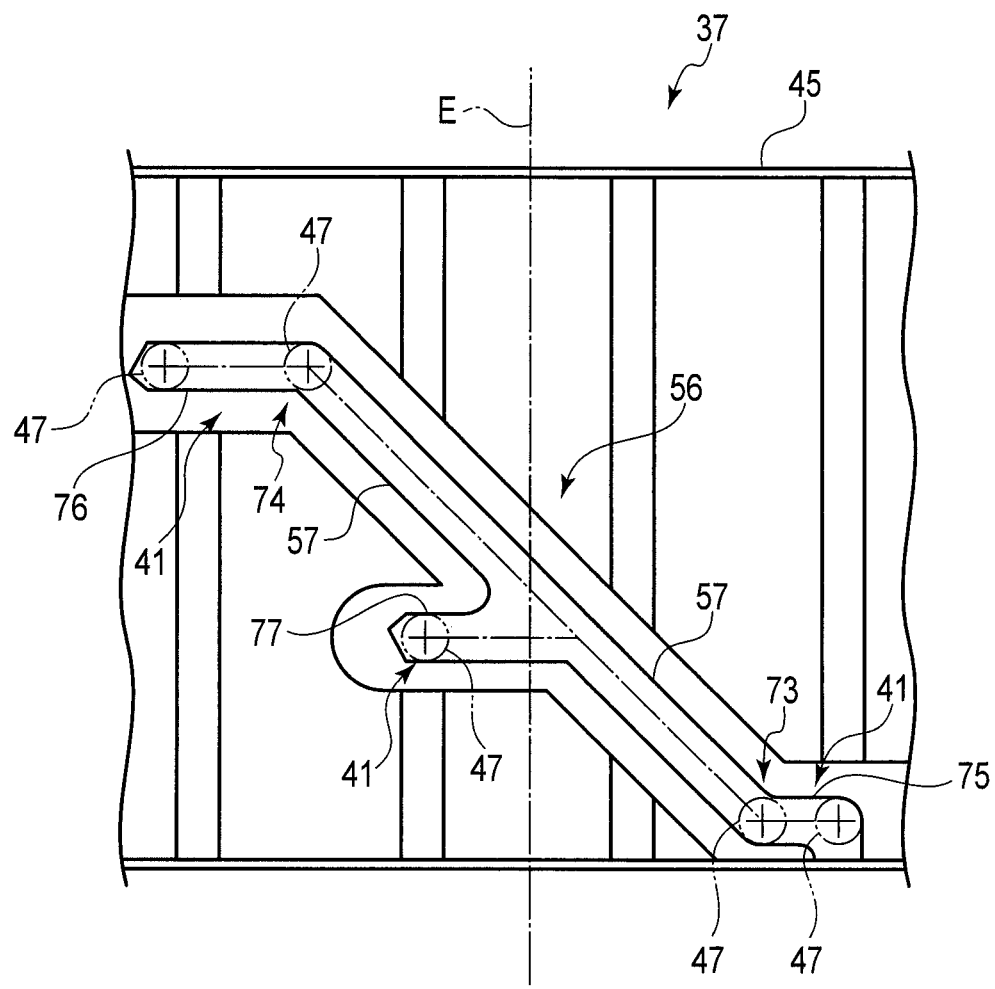
FIG. 18 is a schematic view schematically showing a positioning portion formed on an outer circumferential surface of a dial of an advance and retreat assisting tool of an endoscope system according to an eighth modified example in a state where the outer circumferential surface of the dial is developed in a plane.

An endoscope system according to an eighth modified example will be described with reference to FIG. 18. In the present modified example, a position at which a positioning portion is provided and a structure of the positioning portion are different from those in the above embodiment and the above modified examples.

In the present modified example, the positioning portion 41 is provided in the dial 45 rather than in the groove of the first cylinder 35. More specifically, the positioning portion 41 is formed as a plurality of grooves that are in communication with a cam groove 57 formed in the dial 45. FIG. 18 is a view schematically showing an outer circumferential portion of the dial 45 formed in an approximately cylindrical shape in a state where the outer circumferential portion of the dial 45 is developed in a plane. The cam groove 57 has a first end portion 73 positioned adjacent to the base 33 and a second end portion 74 positioned on an opposite side of the base 33.

The positioning portion 41 has a first holding portion 75 formed so as to be in communication with the first end portion 73 and having a groove shape, a second holding portion 76 formed so as to be in communication with the second end portion 74 and having a groove shape, and a third holding portion 77 formed at an intermediate position between the first end portion 73 and the second end portion 74 so as to be in communication with the cam groove 57 and having a groove shape. The positioning portion 41 (the first holding portion 75, the second holding portion 76, and the third holding portion 77) is provided in a direction orthogonal to an extending direction E of the rotation shaft 55.

An effect of the present modified example will be described with reference to FIG. 18.

When the user wants to advance the treatment instrument 13 or wants to retreat the treatment instrument 13, the user can advance or retreat the treatment instrument 13 by rotating the dial 45 in the clockwise direction or the counterclockwise direction when viewed from the opposite side of the base 33, as in the above embodiment. In the present modified example, further, the user can fixedly hold the second cylinder 36 at the received position by moving the pin 47 into the first holding portion 75. In addition, the user can fixedly hold the second cylinder 36 at the protruding position 61 by moving the pin 47 into the second holding portion 76. Further, the user can fixedly hold the second cylinder 36 at an intermediate position between the received position 62 and the protruding position 61 by moving the pin 47 into the third holding portion 77.

Therefore, according to the present modified example, an effect that is substantially the same as that of the seventh modified example is achieved.

Ninth Modified Example

An endoscope system 11 according to a ninth modified example will be described with reference to FIGS. 19 and 20. In the present modified example, a structure in which a second cylinder 36 covers an outer side of a first cylinder 35 is different from those of the above embodiment and the above modified examples.

In the present modified example, the second cylinder 36 is formed to have an inner diameter larger than an outer diameter of the first cylinder 35, unlike the above embodiment.

An effect of the present modified example will be described with reference to FIGS. 19 and 20.

When the user wants to advance the treatment instrument 13 by further protruding the treatment instrument 13 from the endoscope 12, the user moves the fingers 64 in the direction in which the fingers 64 become distant from the palm surface 63 to rotate the dial 45 in the clockwise direction when viewed from the opposite side to the base 33. As a result, the pin 47 and the second cylinder 36 are moved toward the treatment instrument insertion port 31 (base 33) by an action of the cam groove 57. In this case, the second cylinder 36 covers the outer side of the first cylinder 35. In the present modified example, the second cylinder 36 is received inside the first cylinder 35 at the received position 62. In this case, as shown in FIG. 19, the restoring force of the tension spring of the assisting portion 38 acts to urge the second cylinder 36 toward the base 33, thereby assisting the movement of the second cylinder 36. Therefore, a force for rotating the dial 45 in the clockwise direction is reduced. As a result, even in a case where the user moves the fingers in the direction in which it is ergonomically difficult to apply the force, the rotation of the dial 45 and the advance of the treatment instrument 13 are assisted by an action of the assisting portion 38.

On the other hand, when the user wants to retreat the treatment instrument 13 so as to return the treatment instrument 13 toward the endoscope 12, the user moves the fingers 64 in the direction in which the fingers 64 approach the palm surface 63 to rotate the dial 45 in the counterclockwise direction when viewed from the opposite side to the base 33. As a result, the pin 47 and the second cylinder 36 are moved toward the opposite side (protruding position 61) to the treatment instrument insertion port 31 by an action of the cam groove 57. In the present modified example, the second cylinder 36 protrudes toward a distal end side of the first cylinder 35 at the protruding position 61. In this case, as shown in FIG. 20, the restoring force of the tension spring of the assisting portion 38 becomes a resistance of the movement of the second cylinder 36. However, since an operation of moving the fingers in the direction in which the fingers approach the palm surface 63 is an operation in which it is ergonomically easy to apply a force, the rotation of the dial 45 in the counterclockwise direction (retreat of the treatment instrument 13) is hardly hindered. In this example, the movement between the protruding position 61 and the received position 62 has been described by way of example, but the same effect is also achieved in the movement at an intermediate position between the protruding position 61 and the received position 62.

According to the present modified example, in the advance and retreat assisting tool 14 for a treatment instrument, the inner diameter of the second cylinder 36 is larger than the outer diameter of the first cylinder 35, and the second cylinder 36 is advanced and retreated between a position in a state where the first cylinder 35 is inserted into the second cylinder 36 and a position in a state where the first cylinder 35 protrudes from the second cylinder 36. According to such a configuration, it is possible to realize a configuration in which the second cylinder 36 moves with respect to the first cylinder 35 with a simple structure.

Tenth Modified Example

An endoscope system according to a tenth modified example will be described with reference to FIGS. 21 to 26. In the present modified example, a structure in which a second cylinder 36 is moved with respect to a first cylinder 35 and a configuration and a disposition of an assisting portion 38 are different from those of the above embodiment and the above modified examples.

Figure 24:
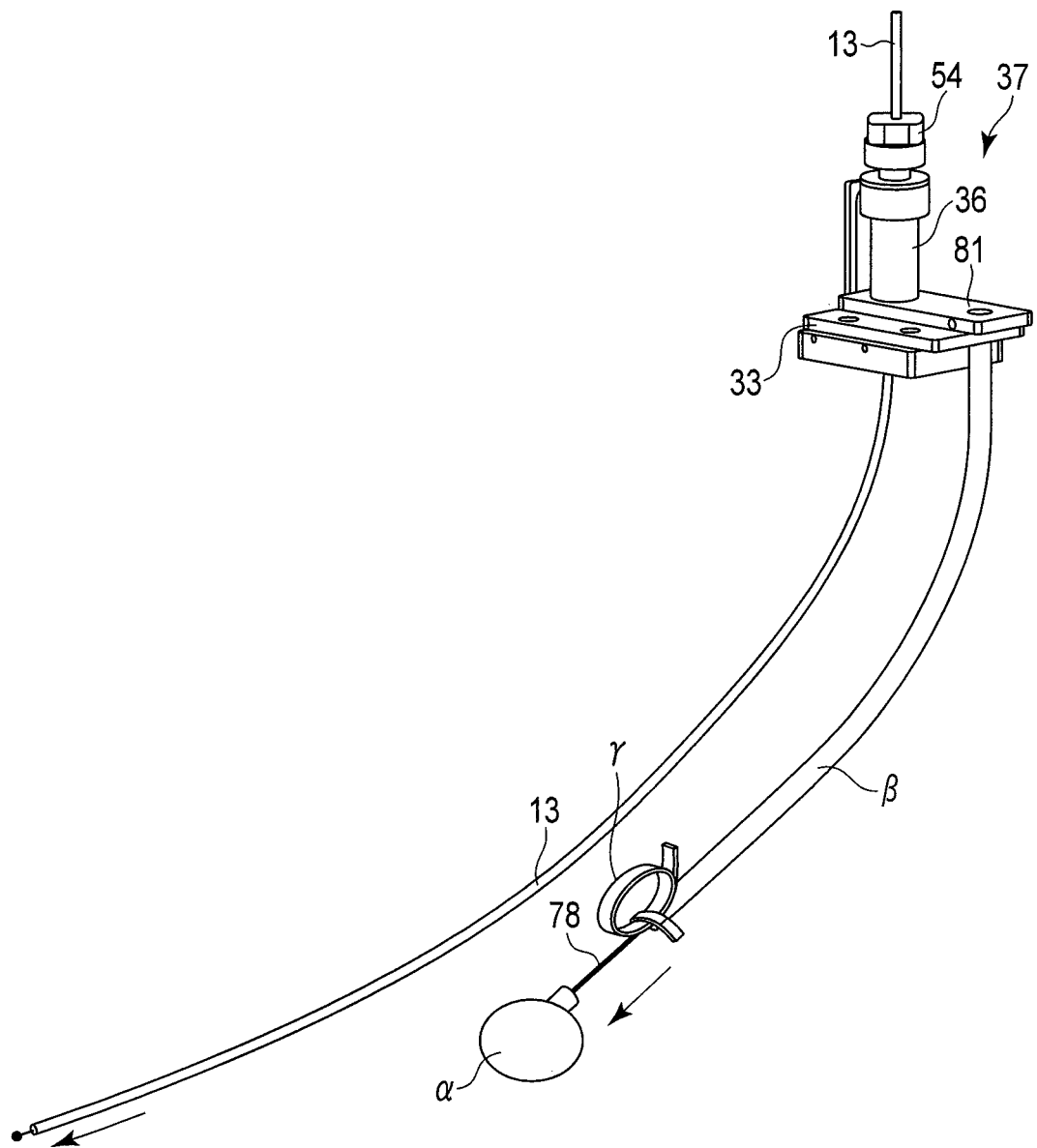
FIG. 24 is a perspective view showing the advance and retreat assisting tool of the endoscope system according to the tenth modified example.
Figure 25:
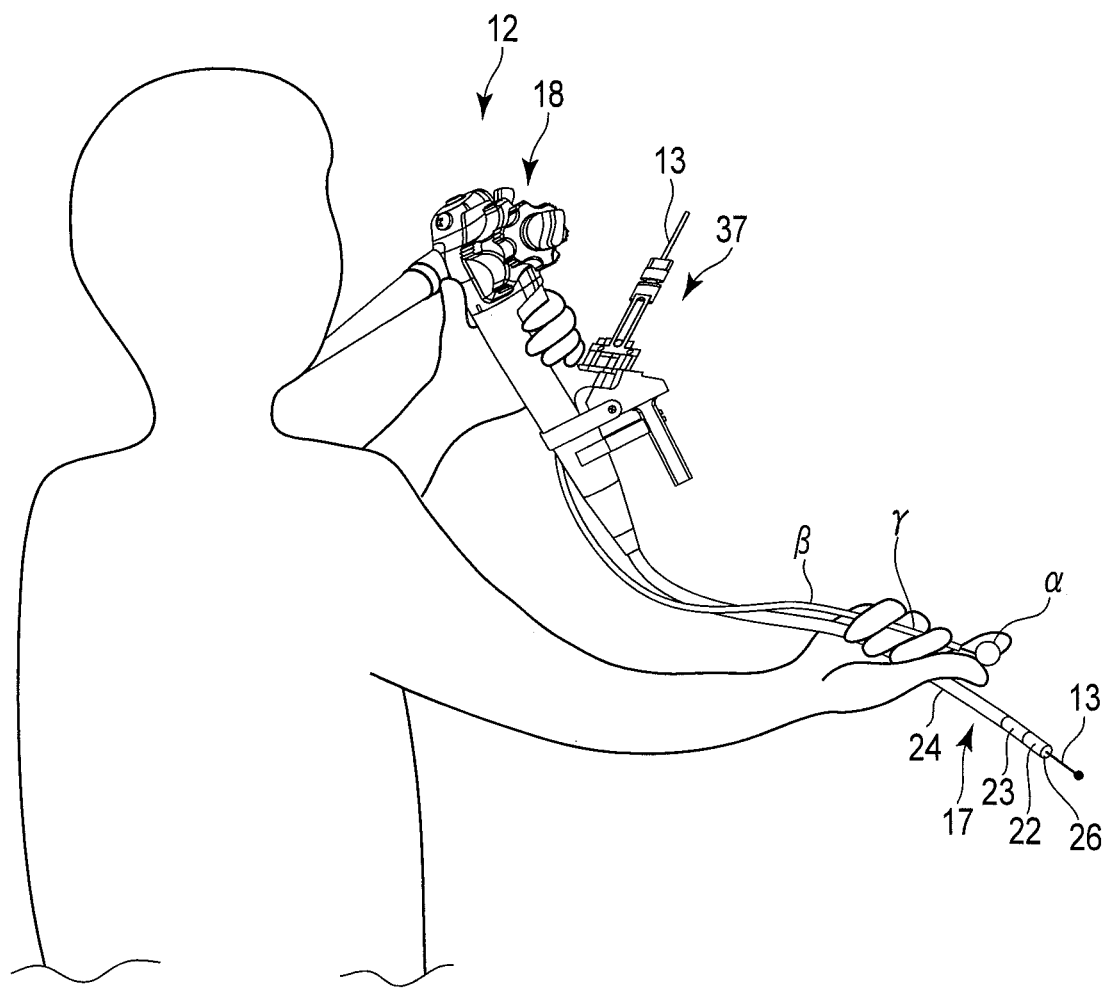
FIG. 25 is a schematic view showing a state where a grasp portion is grasped with a left hand of an operator, a long portion and a flexible tube portion are grasped with a right hand of the operator, and a long operation portion is grasped with the right hand of the operator, in an endoscope to which the advance and retreat assisting tool according to the tenth modified example is attached.
Figure 26:
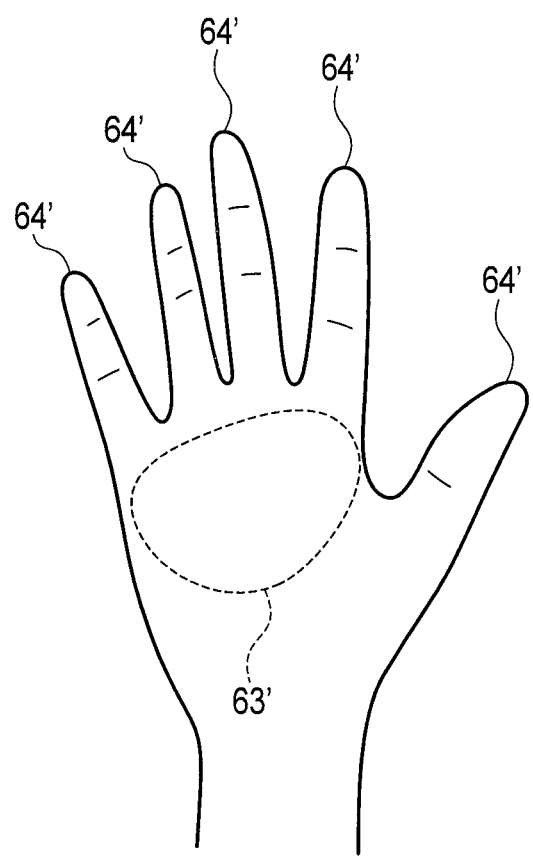
FIG. 26 is a front view showing a position relationship between fingers and a palm surface (palm) of a right hand.

A long portion 78 has a length from the treatment instrument insertion portion 31 to the distal end constituting portion 22 of the insertion portion 17, and is arranged from the treatment instrument insertion port 31 to the side of the distal end constituting portion 22 of the insertion portion 17. The long portion 78 has a longitudinal axis. The second cylinder 36 can be advanced and retreated between the protruding position 61 and the received position 62 with respect to the first cylinder 35 through the long portion 78 and a long portion fixing portion 81 fixing one end of the long portion 78 and the second cylinder 36 to each other. The long portion 78 is pulled from the operation portion 18 toward the distal end constituting portion 22 to be advanced along a longitudinal axis direction of the long portion 78. As a result, the long portion 78 moves toward the received position 62 with respect to the first cylinder 35 through the long portion fixing portion 81 (see FIG. 22). In addition, the long portion 78 is pushed back from the distal end constituting portion 22 to the operation portion 18, so that the long portion 78 is retreated along the longitudinal axis direction of the long portion 78. As a result, the long portion 78 moves to the protruding position 61 with respect to the first cylinder 35 through the long portion fixing portion 81 (see FIG. 21). In order to advance and retreat the long portion 78, the advance and retreat assisting tool 14 has a long operation portion α at one end of the long portion 78. As shown in FIGS. 24 and 25, the long operation portion α functions as, for example, a knob held by an operator. Further, the advance and retreat assisting tool 14 has a long guide member β guiding the long portion 78 by allowing the long portion 78 to be inserted into the long guide member. The long guide member β is formed as an elongated cylindrical member into which the long portion 78 is inserted. The long guide member β is shorter than the long portion 78. The long guide member β is arranged from the base 33 to the tube portion 24 of the insertion portion 17. In addition, the long guide member β has flexibility. The long guide member β is fixed to the base 33. The long guide member β has a finger insertion portion γ (see FIG. 24) into which any one of fingers 64' of an operator's hand is inserted in a state (see FIG. 25) where the operator grasps the long portion 78 including the long guide member β and grips the long operation portion α with any one (see FIG. 26) of the fingers 64' of his/her hand. The finger insertion portion γ is a belt-shaped member having a ring shape. The long operation portion α may have a ring shape into which any one (see FIG. 26) of the fingers 64' of the operator's hand can be inserted. In addition, a size relationship between the first cylinder 35 and the second cylinder 36 is the same as that of the ninth modified example.

Figure 23:
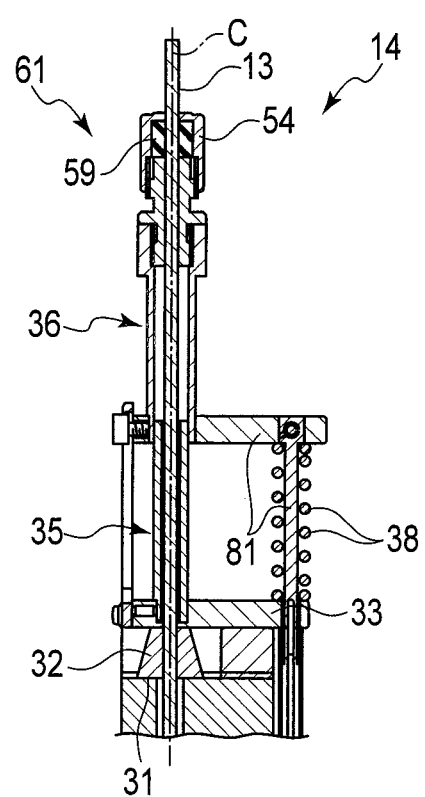
FIG. 23 is a cross-sectional view showing an advance and retreat assisting tool of an endoscope system according to a further modification of the tenth modified example in a state where a second cylinder is at a protruding position.

As shown in FIG. 21, the assisting portion 38 is formed of a tension spring (tension coil spring) spanned between the base 33 and the second cylinder 36. As a further modification of the present modified example, the assisting portion 38 may be formed of a compression spring (compression coil spring) interposed between the base 33 and the second cylinder 36. In this case, one end of the assisting portion 38 is fixed to the base 33, and the other end of the assisting portion 38 is fixed to the second cylinder 36. Alternatively, as a further modification of the present modified example, the assisting portion 38 may be formed of a tension spring (tension coil spring) spanned between a wire fixing portion 81 and the base 33, as shown in FIG. 23. Alternatively, in FIG. 23, the assisting portion 38 may be formed of a compression spring (compression coil spring) interposed between the wire fixing portion 81 and the base 33. In this case, one end of the assisting portion 38 is fixed to the base 33, and the other end of the assisting portion 38 is fixed to the wire fixing portion 81. The assisting portion 38 is disposed outside the first cylinder 35.

The movement from the protruding position 61 to the received position 62 is to move the fingers 64' in a direction in which the fingers 64' become distant from a palm surface 63', which is a direction in which it is ergonomically difficult to apply a force, but is a direction in which an urging force of the assisting portion 38 is generated, and thus, sliding of the long portion 78 is assisted. According to such a configuration, it is possible to realize the advance and retreat assisting tool 14 for a treatment instrument in which user's operability is improved. On the other hand, the movement from the received position 62 to the protruding position 61 is to move the fingers 64' in a direction in which the fingers 64' approach the palm surface 63', which is an operation in which it is ergonomically easy to apply a force, and thus, sliding of the long portion 78 is not hindered by the assisting portion 38.

According to the present modified example, the same effect as that of the ninth modified example is achieved.

Eleventh Modified Example

An endoscope system 11 according to an eleventh modified example will be described with reference to FIG. 27. In the present modified example, a structure in which a cam groove 57 is formed on an inner circumferential surface of a dial 45 and a configuration and a disposition of an assisting portion 38 are different from those in the above embodiment and the above modified examples.

The advance and retreat mechanism 37 includes a dial 45 and a cam mechanism 56 (transfer portion) converting rotation of the dial 45 into advance and retreat of the second cylinder 36 (treatment instrument 13). The dial 45 is provided so as to be rotatable around the first cylinder 35 using the first cylinder 35 as a rotation shaft. An axial center of the first cylinder 35 that becomes the rotation axis coincides with the center axis C of the treatment instrument 13. The cam mechanism 56 includes a cam groove 57 formed in a spiral shape on an inner circumferential surface of the dial 45 and a pin 47 formed in the second cylinder 36 so as to protrude from the second main body 51. For this reason, the dial 45 is rotated by the user's fingers 64, so that the second cylinder 36 can protrude from the first cylinder 35 or the second cylinder 36 can be received in the first cylinder 35, by an action of the cam mechanism 56 (the cam groove 57 and the pin 47). Therefore, the advance and retreat mechanism 37 can advance and retreat the treatment instrument 13 by rotating the dial 45 with the user's fingers. That is, when viewed from the opposite side to the base 33, when the dial 45 is rotated clockwise, the pin 47 is moved toward the opposite side to the base 33 by an action of the cam groove 57. Likewise, when viewed from the opposite side to the base 33, when the dial 45 is rotated counterclockwise, the pin 47 is moved toward the base 33 by an action of the cam groove 57.

The assisting portion 38 is formed of a tension spring (tension coil spring) spanned between the base 33 and the second cylinder 36. As a further modification of the present modified example, the assisting portion 38 may be formed of a compression spring (compression coil spring) interposed between the base 33 and the second cylinder 36. In this case, one end of the assisting portion 38 is fixed to the base 33, and the other end of the assisting portion 38 is fixed to the second cylinder 36. The assisting portion 38 may also be spanned between the first cylinder 35 and the second cylinder 36. The assisting portion 38 is disposed within the first cylinder 35 and inside the dial 45.

According to the present modified example, the same effect as that of the first embodiment is achieved. Alternatively, as a further modification of the eleventh modified example, as shown in FIGS. 28 and 29, the assisting portion 38 (tension spring) may be provided outside the first cylinder 35 and the dial 45. As a further modification in FIGS. 28 and 29, the assisting portion 38 may be formed of a compression spring (compression coil spring). FIG. 28 corresponds to a state where the second cylinder 36 is at the protruding position 61. FIG. 29 corresponds to a state where the second cylinder 36 is at the received position 62. According to such a further modified example, the same effect as that of the above embodiment is achieved.

Twelfth Modified Example

An endoscope system 11 according to a twelfth modified example will be described with reference to FIG. 30. In the present modified example, a structure in which a sealing member (O-ring) 84 is disposed between a second cylinder 36 and a third cylinder 83 is different from those of the above embodiment and the above modified examples.

An advance and retreat assisting tool 14 includes a base 33 attached to the operation portion 18, an attaching portion 34 attaching the base 33 to an endoscope 12 such that a through-hole 33A of the base 33 faces a treatment instrument insertion port 31 of the endoscope 12, a first cylinder 35 attached to the base 33, a second cylinder 36 sliding in an advance and retreat direction with respect to the first cylinder 35 along a center axis C of the first cylinder 35, a blocking member 82 attached to the base 33 so as to be positioned inside the second cylinder 36, an advance and retreat mechanism 37 advancing and retreating the second cylinder 36 along the center axis C with respect to the first cylinder 35, an assisting portion 38 assisting rotation of the advance and retreat mechanism 37 when the advance and retreat mechanism 37 is rotated in one direction, and a positioning portion 41 positioning the second cylinder 36 at a predetermined position with respect to the base 33. The first cylinder 35, the second cylinder 36, the blocking member 82, the advance and retreat mechanism 37, and the assisting portion 38 constitute a moving unit 42 for advancing and retreating the treatment instrument 13.

The blocking member 82 includes a third cylinder 83 provided inside the first cylinder 35 and having a cylindrical shape and a sealing member 84 provided in the vicinity of a distal end portion of the third cylinder 83 opposite to the base 33. The third cylinder 83 has an overlap portion 83A overlapping the second cylinder 36 in a state where it is at a protruding position 61 and a groove 85 provided in the overlap portion 83A.

The groove 85 is recessed and formed in an annular shape in an outer circumferential portion of the third cylinder 83 in the overlap portion 83A. The sealing member 84 is disposed inside the groove 85. The sealing member 84 is an O ring formed of a material having rubber-like elasticity such as silicon rubber. The sealing member 84 is interposed between the outer circumferential portion of the third cylinder 83 and an inner circumferential surface of the second cylinder 36. The sealing member 84 can be closely adhered to the inner circumferential surface of the second cylinder 36.

An effect of the present modified example will be described with reference to FIG. 30.

In the present modified example, similar to the above embodiment, the user rotates the dial 45 in the clockwise direction or the counterclockwise direction when viewed from the side opposite to the base 33, thereby moving the second cylinder 36 between the received position 62 and the protruding position 61 with respect to the first cylinder 35. In this case, the sealing member 84 is closely adhered to the inner circumferential surface of the second cylinder 36 regardless of a position of the second cylinder 36. In addition, when the second cylinder 36 moves, the sealing member 84 slides with respect to the inner circumferential surface of the second cylinder 36. Meanwhile, in the second cylinder 36, due to a fixing structure (watertight structure) through a fixing portion 54 and a fastening portion 59, a liquid is prevented from being leaked to the outside of the second cylinder 36 along the treatment instrument 13. For this reason, even though the liquid such as a body fluid of a medical examinee (subject) bleeds along the treatment instrument 13, the leak of the liquid is prevented by the blocking member 82 and the watertight structure through the fixing portion 54 and the fastening portion 59, so that the liquid is not leaked to the outside of the second cylinder 36.

According to the present modified example, the advance and retreat assisting tool 14 for a treatment instrument includes the blocking member 82 abutting on the inner circumferential surface of the second cylinder 36 to block movement of the liquid between the inside of the second cylinder 36 and the outside of the second cylinder 36. According to such a configuration, since the liquid rising along the treatment instrument 13 can be confined to the outside of the second cylinder 36 by the blocking member 82, members disposed in the vicinity of the second cylinder 36 can be maintained in a clean state without being into contact with the liquid.

Second Embodiment

An endoscope system 11 according to a second embodiment will be described with reference to FIGS. 31 to 35. In the endoscope system 11 according to the second embodiment, a structure of an advance and retreat assisting tool 14 is different from of that of the first embodiment, but the other parts are common to those of the first embodiment. In the following, parts different from those of the above embodiment will be mainly described, and illustration or description of parts common to those of the above embodiment will be omitted.

As shown in FIGS. 31 and 32, the advance and retreat assisting tool 14 includes a base 33 attached to an operation portion 18, an attaching portion 34 attaching the base 33 to an endoscope 12 such that a through-hole 33A of the base 33 faces a treatment instrument insertion port 31 of the endoscope 12, a first cylinder 35 attached to the base 33, a second cylinder 36 sliding in an advance and retreat direction with respect to the first cylinder 35 along a center axis C of the first cylinder 35, an advance and retreat mechanism 37 advancing and retreating the second cylinder 36 along the center axis C with respect to the first cylinder 35, an assisting portion 38 assisting rotation of the advance and retreat mechanism 37 when the advance and retreat mechanism 37 rotates in one direction, and a positioning portion 41 positioning the second cylinder 36 at a predetermined position with respect to the base 33. The first cylinder 35, the second cylinder 36, the advance and retreat mechanism 37, the assisting portion 38, and the positioning portion 41 constitute a moving unit 42 for advancing and retreating a treatment instrument 13. The moving unit 42 is attached to the base 33 through a first engaging portion 91 to be described below.

The first cylinder 35 has an insertion portion 86 which is inserted into the through-hole 33A of the base 33, the first engaging portion 91 which is formed on the insertion portion 86, and a pair of receiving portions 92 which are formed in the insertion portion 86 and into which a distal end of a fixing member 65 is fitted. The insertion portion 86 has a cylindrical shape. The pair of receiving portions 92 are formed on an outer circumferential surface of the insertion portion 86. The pair of receiving portions 92 are provided, respectively, on both sides having the first engaging portion 91 sandwiched therebetween. Each of the receiving portions 92 has a groove shape extending in a direction orthogonal to an insertion direction of the insertion portion 86 (a direction of the center axis C of the first cylinder 35).

The first engaging portion 91 is formed as a projection protruding in a radial direction of the first cylinder 35 from a main body of the insertion portion 86. The first engaging portion 91 is also referred to as a projection protruding toward the base 33. In the present embodiment, the first engaging portion 91 is formed as a pair of projections, and this pair of projections function as one long positioning member 93 represented by a two-dot chain line in FIG. 31. The first engaging portion 91 may be provided as a plurality of projection pairs rather than a pair of projections on the insertion portion 86. Alternatively, the first engaging portion 91 may be formed as a recess formed along the radial direction of the first cylinder 35.

The base 33 has the through-hole 33A through which the treatment instrument 13 passes. The base 33 can cover, for example, a forcep plug 32 from an upper side (see FIG. 27 and the like). The base 33 has a second engaging portion 94 capable of receiving the first engaging portion 91 formed in the first cylinder 35 (moving unit 42). The base 33 has a through-hole through which the fixing member 65 (screw) passes.

The second engaging portion 94 can engage with the first engaging portion 91 (the positioning member 93) such that a plurality of positions at which attachment angles of the moving unit 42 to the base 33 are different from each other can be taken stepwise. The second engaging portion 94 is a plurality of concave portions formed along a radial direction of the base 33. In other words, the second engaging portion 94 has a plurality of sets of concave portion pairs along the radial direction of the base 33. As shown in FIG. 32, the second engaging portion 94 can receive the first engaging portion 91 (the positioning member 93) at different angles. In a case where the first engaging portion 91 is formed as the recess along the radial direction of the first cylinder 35, the second engaging portion 94 is formed as a protruding portion (protruding portion engaging with the recess of the first engaging portion 91) protruding toward the center axis (the moving unit 42) of the through-hole 33A.

Figure 35:
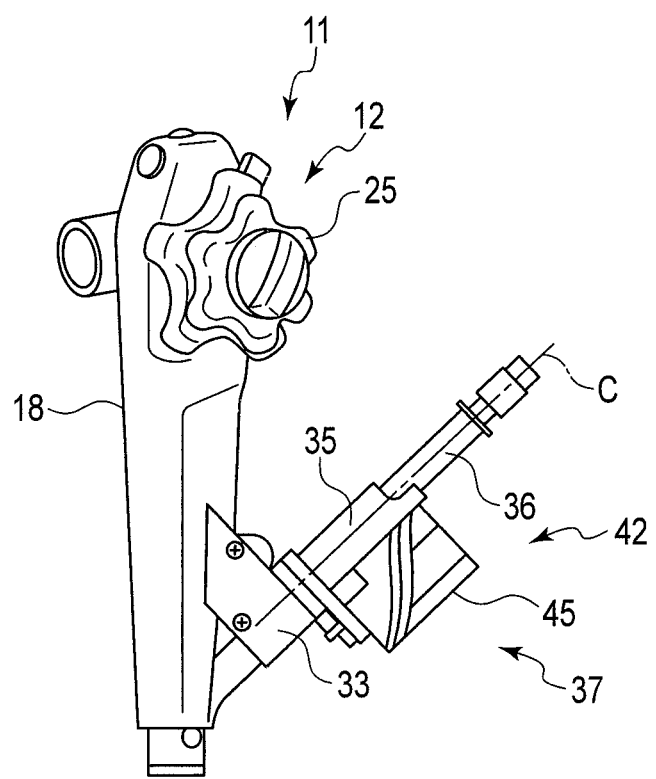
FIG. 35 is a perspective view showing a state where the moving unit of the endoscope system shown in FIG. 31 is at a position distant from the operation portion of the endoscope.

An effect of the endoscope system 11 according to the present embodiment will be described with reference to FIGS. 31 and 35.

Figure 33:
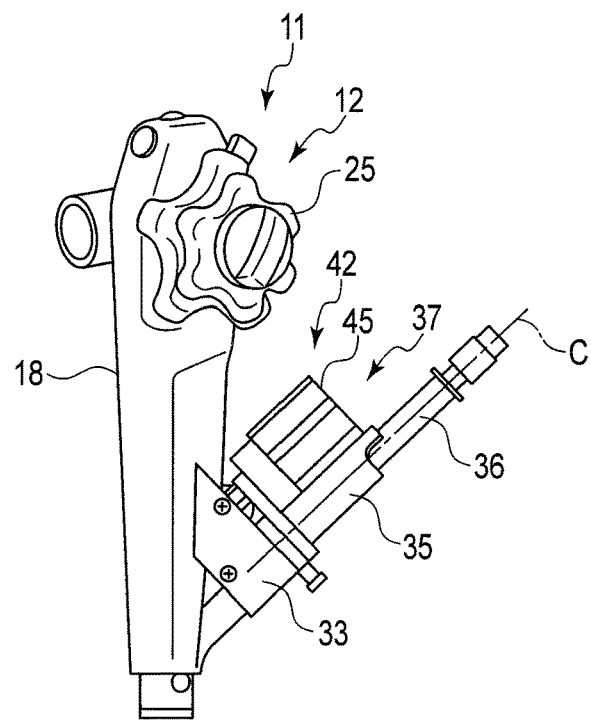
FIG. 33 is a perspective view showing a state where the moving unit of the endoscope system shown in FIG. 31 is at a position close to an operation portion of an endoscope.

As in the first embodiment, it is possible to advance and retreat the second cylinder 36 with respect to the first cylinder 35 by rotating a dial 45 in a clockwise direction or a counterclockwise direction when viewed from an opposite side to the base 33. In the present embodiment, further, it is possible to adjust an attachment angle of the moving unit 42 to the base 33 depending on a size of a user's hand by adjusting an attachment angle of the first engaging portion 91 to the second engaging portion 94. That is, in a case where a user having a relatively small hand uses the endoscope system 11, such as a case where the user is a female doctor, it is possible to dispose the moving unit 42 and the dial 45 at positions close to the operation portion 18 of the endoscope 12, as shown in FIG. 33, by engaging the first engaging portion 91 with the second engaging portion 94 at an appropriate position.

Figure 34:
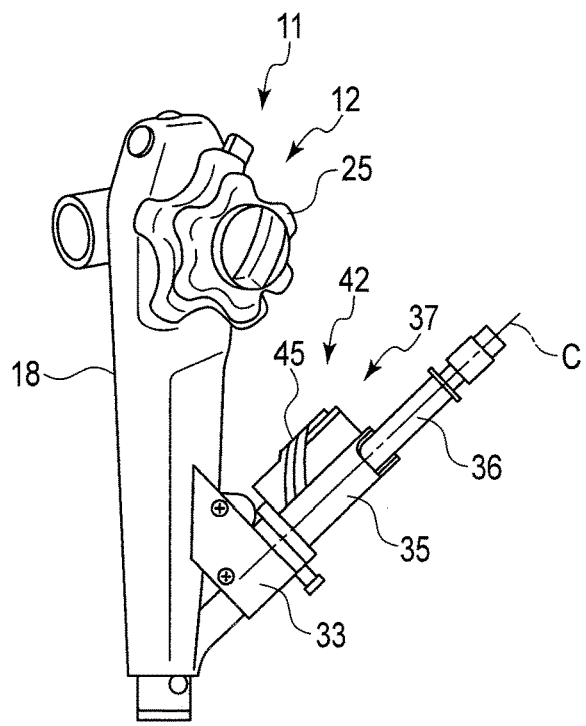
FIG. 34 is a perspective view showing a state where a distance between the moving unit and the operation portion of the endoscope is an intermediate distance, in the endoscope system shown in FIG. 31.

In a case where a user having a relatively large hand uses the endoscope system 11, such as a case the user is a large doctor, it is possible to make a distance between the moving unit 42 and the operation portion 18 of the endoscope 12 an intermediate distance (general length), as shown in FIG. 34, by engaging the first engaging portion 91 with the second engaging portion 94 at an appropriate position. In a case where an advance and retreat operation of the treatment instrument 13 is not performed by the advance and retreat assisting tool 14 for a treatment instrument, it is possible to dispose the moving unit 42 and the dial 45 at positions distant from the operation portion 18 of the endoscope 12, as shown in FIG. 35, by engaging the first engaging portion 91 with the second engaging portion 94 at an appropriate position.

According to the present embodiment, the advance and retreat assisting tool 14 for a treatment instrument can be configured as follows. The advance and retreat assisting tool 14 for a treatment instrument includes the base 33 which is attached to the endoscope 12, the moving unit 42 which is attached to the base 33 through the first engaging portion 91 and advances and retreats the treatment instrument passing through the inside of the endoscope 12, and the second engaging portion 94 which is provided in the base 33 and engages with the first engaging portion 91 such that the plurality of positions at which the attachment angles of the moving unit 42 to the base 33 are different from each other can be taken stepwise.

According to such a configuration, it is possible to allow the moving unit 42 to approach the endoscope 12 and allow the moving unit 42 to become distant from the endoscope 12. As a result, it is possible to provide the advance and retreat assisting tool 14 for a treatment instrument easily used by a user regardless of a size of a user's hand. In addition, since it is possible to change the attachment angle of the moving unit 42 stepwise, it is possible to realize the advance and retreat assisting tool 14 for a treatment instrument easily used by the user by disposing the moving unit 42 at an appropriate position depending on the size of the user's hand. Further, in the case where the advance and retreat operation of the treatment instrument 13 is not performed by the advance and retreat assisting tool 14 for a treatment instrument, it is possible to dispose the moving unit 42 at the position distant from the operation portion 18 so as not to disturb an operation of the endoscope 12.

The first engaging portion 91 is any one of the projection protruding toward the base 33 and the recess formed along the radial direction of the moving unit 42. The second engaging portion 94 is the concave portion with which the projection engages when the first engaging portion 91 is the projection. The second engaging portion 94 is the protruding portion engaging with the recess when the first engaging portion 91 is the recess.

According to such a configuration, it is possible to realize the advance and retreat assisting tool 14 for a treatment instrument in which the attachment angle of the moving unit 42 can be changed by a simple structure using the projection and the concave portion or the recess and the protruding portion. As a result, it possible to realize the advance and retreat assisting tool for a treatment instrument easily used by the user regardless the size of the user's hand without extremely increasing the manufacturing cost of the advance and retreat assisting tool 14 for a treatment instrument.

Several embodiments have been specifically described hereinabove with reference to the drawings, but the present invention is not limited to the abovementioned embodiments, and can be embodied by modifying components without departing from the gist of the present invention. In each of the above embodiments and modified examples, the assisting portion 38 is formed of the spring. However, the assisting portion 38 is not limited to the spring, and may be an elastic member, a damper, or the like having rubber-like elasticity. In addition, it is possible to realize one endoscope system 11 or advance and retreat assisting tool 14 for a treatment instrument by appropriately combining the components in the abovementioned different embodiments with each other.

The applicant also recognizes structures described below as an invention.

[1] An advance and retreat assisting tool for a treatment instrument including:

a base which is attached to an endoscope, a moving unit which is attached to the base through a first engaging portion and advances and retreats the treatment instrument passing through an inside of the endoscope, and a second engaging portion which is provided in the base and engages with the first engaging portion such that a plurality of positions at which attachment angles of the moving unit to the base are different from each other can be taken stepwise.

[2] The advance and retreat assisting tool for a treatment instrument according to [1], wherein the first engaging portion is any one of a projection protruding toward the base and a recess provided in the moving unit, and the second engaging portion is a concave portion with which the projection engages when the first engaging portion is the projection, or the second engaging portion is a protruding portion engaging with the recess when the first engaging portion is the recess.

REFERENCE SIGNS LIST 11 endoscope system
12 endoscope
13 treatment instrument
14 advance and retreat assisting tool
33 base
33A through-hole
34 attaching portion
35 first cylinder
36 second cylinder
37 advance and retreat mechanism
38 assisting portion
41 positioning portion
42 moving unit
45 dial
47 pin
55 rotation shaft
56 cam mechanism
63 palm surface
64 finger
91 first engaging portion
94 second engaging portion

The invention claimed is:

1. An advance and retreat assisting tool for a treatment instrument, comprising:

a base which has a through-hole;

a first cylinder which is attached to the base such that an inner portion thereof is in communication with the through-hole;

a second cylinder which has a clamp for fixing the treatment instrument to the second cylinder, the second cylinder being configured to slide in an advance and retreat direction with respect to the first cylinder along a center axis of the first cylinder;

an advance and retreat mechanism configured to convert a rotation to an advance and retreat of the second cylinder along the center axis with respect to the first cylinder; and a spring configured to urge the second cylinder in a predetermined direction along the center axis with respect to the base with an urging force smaller than a resistance force when the second cylinder slides and to assist the rotation of the advance and retreat mechanism when the advance and retreat mechanism rotates in one direction.

2. The advance and retreat assisting tool for a treatment instrument according to claim 1, wherein the resistance force when the second cylinder slides includes at least one of a frictional force between the first cylinder and the second cylinder and a frictional force applied when the advance and retreat mechanism advances or retreats the second cylinder.

3. The advance and retreat assisting tool for a treatment instrument according to claim 1, further comprising a positioning portion which positions the urged second cylinder at a predetermined position with respect to the base.

4. The advance and retreat assisting tool for a treatment instrument according to claim 3, wherein the positioning portion defines a relative positional relationship between the first cylinder and the second cylinder in a direction of the center axis.

5. The advance and retreat assisting tool for a treatment instrument according to claim 4, wherein the positioning portion is provided between the first cylinder and the second cylinder, and defines the relative positional relationship between the first cylinder and the second cylinder in the direction of the center axis in a plurality of steps.

6. The advance and retreat assisting tool for a treatment instrument according to claim 1, wherein an outer diameter of the second cylinder is smaller than an inner diameter of the first cylinder, and the second cylinder advances and retreats between a position in a state where the second cylinder is inserted into the first cylinder and a position in a state where the second cylinder protrudes from the first cylinder.

7. The advance and retreat assisting tool for a treatment instrument according to claim 6, further comprising a blocking member which abuts on an inner circumferential surface of the second cylinder to block movement of a liquid between an inside of the second cylinder and an outside of the second cylinder.

8. The advance and retreat assisting tool for a treatment instrument according to claim 7, wherein the blocking member includes:

a third cylinder which is positioned inside the first cylinder and has a portion overlapping the second cylinder; and a sealing member which is interposed between an outer circumferential portion of the third cylinder and the inner circumferential surface of the second cylinder in the overlapping portion.

9. The advance and retreat assisting tool for a treatment instrument according to claim 1, wherein an inner diameter of the second cylinder is smaller than an outer diameter of the first cylinder, and the second cylinder advances and retreats between a position in a state where the first cylinder is inserted into the second cylinder and a position in a state where the first cylinder protrudes from the second cylinder.

10. The advance and retreat assisting tool for a treatment instrument according to claim 1, wherein
the advance and retreat mechanism includes:
a dial which rotates around a predetermined rotation shaft by a force operated from the outside; and
a transfer portion which converts a rotation force of the dial into a force for advancing and retreating the second cylinder in a direction along the center axis.

11. The advance and retreat assisting tool for a treatment instrument according to claim 10, wherein the rotation shaft extends in a direction along an extending direction of the treatment instrument.

12. The advance and retreat assisting tool for a treatment instrument according to claim 10, wherein an axial center of the rotation shaft coincides with a center axis of the treatment instrument.

13. The advance and retreat assisting tool for a treatment instrument according to claim 1, further comprising an attaching portion configured to attach the base to an endoscope such that the through-hole faces a treatment instrument insertion port of the endoscope.

14. The advance and retreat assisting tool for a treatment instrument according to claim 1, wherein the spring comprises one of a tension spring and a compression spring.

15. The advance and retreat assisting tool for a treatment instrument according to claim 1, wherein the clamp comprises:
a cap fixed to an end of the second cylinder; and
an elastic material having an opening through which the treatment instrument passes;
wherein the cap is configured to compress the elastic material to reduce a size of the opening such that the treatment tool is clamped in the hole.

16. An endoscope system comprising:
an endoscope having a channel accessible via a treatment instrument insertion port; and
an advance and retreat assisting tool attached to the treatment instrument insertion port, the advance and retreat assisting tool comprising:
a base which has a through-hole;
a first cylinder which is attached to the base such that an inner portion thereof is in communication with the through-hole;
a second cylinder which has a clamp for fixing a treatment instrument to the second cylinder, the second cylinder being configured to slide in an advance and retreat direction with respect to the first cylinder along a center axis of the first cylinder;
an advance and retreat mechanism configured to convert a rotation to an advance and retreat of the second cylinder along the center axis with respect to the first cylinder; and
a spring configured to urge the second cylinder in a predetermined direction along the center axis with respect to the base with an urging force smaller than a resistance force when the second cylinder slides and to assist the rotation of the advance and retreat mechanism when the advance and retreat mechanism rotates in one direction.

17. An advance and retreat assisting tool for a treatment instrument, comprising:
a first cylinder;
a second cylinder which has a clamp for fixing the treatment instrument to the second cylinder, the second cylinder being configured to slide in an extending direction of the first cylinder with respect to the first cylinder;
an advance and retreat mechanism configured to slide the second cylinder in the extending direction of the first cylinder; and
a spring configured to assist the sliding of the second cylinder with respect to the first cylinder when the advance and retreat mechanism is operated in a first direction.

18. The advance and retreat assisting tool for a treatment instrument according to claim 17, further comprising an attaching portion configured to attach the base to an endoscope such that the through-hole faces a treatment instrument insertion port of the endoscope.

19. The advance and retreat assisting tool for a treatment instrument according to claim 17, wherein the spring comprises one of a tension spring and a compression spring.

20. The advance and retreat assisting tool for a treatment instrument according to claim 17, wherein the clamp comprises:
a cap fixed to an end of the second cylinder; and
an elastic material having an opening through which the treatment instrument passes;
wherein the cap is configured to compress the elastic material to reduce a size of the opening such that the treatment tool is clamped in the hole.

* * * * *